US012606803B2

(12) United States Patent
Zuckermann et al.

(10) Patent No.: US 12,606,803 B2
(45) Date of Patent: Apr. 21, 2026

(54) METHODS FOR GROWING AFRICAN SWINE FEVER VIRUS IN FETAL PORCINE LUNG ALVEOLAR MACROPHAGE CELLS

(71) Applicants: Aptimmune Biologics, Inc., St. Louis, MO (US); The Board of Trustees of the University of Illinois, Urbana, IL (US)

(72) Inventors: Federico A. Zuckermann, Champaign, IL (US); Linda Kathleen Dixon, Surrey (GB); Maria Raquel Seica Portugal, Surrey (GB); Lynnette Claire Goatley, Hampshire (GB)

( * ) Notice: Subject to any disclaimer, the term of this patent is extended or adjusted under 35 U.S.C. 154(b) by 1134 days.

(21) Appl. No.: 17/626,415

(22) PCT Filed: Jul. 13, 2020

(86) PCT No.: PCT/US2020/041762
§ 371 (c)(1),
(2) Date: Jan. 11, 2022

(87) PCT Pub. No.: WO2021/007572
PCT Pub. Date: Jan. 14, 2021

(65) Prior Publication Data
US 2022/0259569 A1 Aug. 18, 2022

Related U.S. Application Data

(60) Provisional application No. 62/952,889, filed on Dec. 23, 2019, provisional application No. 62/873,075, filed on Jul. 11, 2019.

(51) Int. Cl.
| | |
|---|---|
| *C12N 7/00* | (2006.01) |
| *A61K 39/12* | (2006.01) |
| *A61P 31/20* | (2006.01) |
| *C12N 5/0786* | (2010.01) |
| *G01N 33/569* | (2006.01) |
| *A61K 39/00* | (2006.01) |
| *C12R 1/91* | (2006.01) |

(52) U.S. Cl.
CPC ............... *C12N 7/00* (2013.01); *A61K 39/12* (2013.01); *A61P 31/20* (2018.01); *C12N 5/0645* (2013.01); *G01N 33/56983* (2013.01); *A61K 2039/5254* (2013.01); *A61K 2039/552* (2013.01); *C12N 2710/12021* (2013.01); *C12N 2710/12034* (2013.01); *C12N 2710/12051* (2013.01); *C12N 2710/12071* (2013.01); *C12R 2001/91* (2021.05); *G01N 2333/01* (2013.01)

(58) Field of Classification Search
None
See application file for complete search history.

(56) References Cited

U.S. PATENT DOCUMENTS

| | | | |
|---|---|---|---|
| 8,202,717 | B2 | 6/2012 | Zuckermann |
| 9,474,797 | B1 | 10/2016 | Borca et al. |
| 9,808,520 | B1 | 11/2017 | Borca et al. |
| 2015/0165018 | A1 | 6/2015 | Rodriguez et al. |
| 2016/0115452 | A1* | 4/2016 | Zuckermann ........... A61P 37/00 |
| | | | 435/235.1 |

FOREIGN PATENT DOCUMENTS

| | | |
|---|---|---|
| CN | 101668846 A | 3/2010 |
| CN | 106459931 A | 2/2017 |
| CN | 109952310 A | 6/2019 |
| JP | 2012529892 A | 11/2012 |
| JP | 2017500029 A | 1/2017 |
| WO | 2008089094 A2 | 7/2008 |

OTHER PUBLICATIONS

Carrascosa et al., Current protocols in Cell Biology 2011 Supp 53, pp. 26, 14, 1 to 26.14.25 (Year: 2011).*
Extended European Search Report; European Patent Office; European Application No. 207439480; Feb. 28, 2022; 8 pages.
Canadian Office Action; Canadian Intellectual Property Office; Canadian Application No. 3,146,409; Mar. 21, 2024; 5 pages.
Revilla Y et al., "African Swine Fever Virus Biology and Vaccine Approaches", Adv. Virus Res., 100, pp. 41-74, Epub Nov. 21, 2017 (Nov. 21, 2017).
Chinese First Office Action, China National Intellectual Property Administration, Chinese Application No. 202080001530.1, Jun. 18, 2024, 8 pages.
Chinese Search Report, China National Intellectual Property Administration, Chinese Application No. 202080001530.1, Jun. 17, 2024, 4 pages.
Patricia de León, Laboratory methods to study African swine fever virus, Virus Research, Dec. 31, 2013, 173, pp. 168-179.
Raquel Portugal, A porcine macrophage cell line that supports high levels of replication of OURT88/3, an attenuated strain of African swine fever virus, Emerging Microbes & Infections, Jun. 9, 2020, 9, pp. 1245-1253.
Japanese Office Action, Japan Patent Office, Japanese Application No. 2022-500830, Jun. 25, 2024, 11 pages.
Carrascosa, "Methods for Growing and Titrating African Swine Fever Virus: Field and Laboratory Samples", Current Protocols In Cell Biology, vol. 53, No. 1, Dec. 1, 2011.
Yim-Im, W., H. Huang, and J. Park. "Comparison of PRRSV isolation from clinical samples using MARC-145 and ZMAC cell lines." Conference of Research Workers in Animal Diseases. vol. 105. 2017.

(Continued)

*Primary Examiner* — Shanon A. Foley
*Assistant Examiner* — Myron G Hill
(74) *Attorney, Agent, or Firm* — Taft Stettinius & Hollister LLP

(57) ABSTRACT

A method for generating progeny of an African swine fever (ASF) virus includes providing an isolated or purified fetal porcine lung alveolar macrophage cell capable of replicating the ASF virus, wherein the cell is cultured for at least 5 passages; exposing the cell to the ASF virus; and allowing the ASF virus to replicate in the cell; thereby generating progeny of the ASF virus.

20 Claims, 12 Drawing Sheets

(56)          References Cited

OTHER PUBLICATIONS

European Office Action, European Patent Office, European Application No. 20743948.0, May 16, 2024, 6 pages.

International Search Report and Written Opinion of the International Searching Authority; ISA/US; International Application No. PCT/US2020/041762; Dec. 1, 2020; 13 pages.

Carrascosa et al.; Production and titration of African swine fever virus in porcine alveolar macrophages; Journal of Virological Methods; 1982; pp. 303-310; vol. 3.

International Preliminary Report on Patentability; IThe International Bureau of WIPO; International Application No. PCT/US2020/041762; Jan. 11, 2022; 8 pages.

McCullough KC, Basta S, Knotig S, Gerber H, Schaffner R, et al. 1999. Intermediate stages in monocyte-macrophage differentiation modulate phenotype and susceptibility to virus infection. Immunology 98: 203-12.

Calzada-Nova G, Husmann RJ, Schnitzlein WM, Zuckermann FA. 2012. Effect of the host cell line on the vaccine efficacy of an attenuated porcine reproductive and respiratory syndrome virus. Veterinary Immunology and Immunopathology 148: 116-25.

Chen WY, Schniztlein WM, Calzada-Nova G, Zuckermann FA. 2018. Genotype 2 Strains of Porcine Reproductive and Respiratory Syndrome Virus Dysregulate Alveolar Macrophage Cytokine Production via the Unfolded Protein Response. Journal of Virology 92.

Villeda CJ, Williams SM, Wilkinson PJ, Vinuela E. 1993. Hemostatic abnormalities in African swine fever—A comparison of 2 virus strains of different virulence (Dominicam Republic and Malta 78). Archives of Virology 130: 71-83.

Chapman DAG, Darby AC, Da Silva M, Upton C, Radford AD, Dixon LK. 2011. Genomic Analysis of Highly Virulent Georgia 2007/1 Isolate of African Swine Fever Virus. Emerging Infectious Diseases 17: 599-605.

Chapman DAG, Tcherepanov V, Upton C, Dixon LK. 2008. Comparison of the genome sequences of nonpathogenic and pathogenic African swine fever virus isolates. Journal of General Virology 89: 397-408.

Haresnape JM, Wilkinson PJ, Mellor PS. 1988. Isolation of African swine fever virus from ticks of the Ornithodoros moubata complex (Ixodoidea Argasidae) collected within the African swine fever enzootic area of Malawi. Epidemiology and Infection 101: 173-85.

Nix RJ, Gallardo C, Hutchings G, Blanco E, Dixon LK. 2006. Molecular epidemiology of African swine fever virus studied by analysis of four variable genome regions. Archives of Virology 151: 2475-94.

Alvarez B, Sanchez C, Bullido R, Marina A, Lunney J, et al. 2000. A porcine cell surface receptor identified by monoclonal antibodies to SWC3 is a member of the signal regulatory protein family and associates with protein- tyrosine phosphatase SHP-1. Tissue Antigens 55: 342-51.

Haverson K, Saalmuller A, Alvarez B, Alonso F, Bailey M, et al. 2001. Overview of the Third International Workshop on Swine Leukocyte Differentiation Antigens. Veterinary Immunology and Immunopathology 80: 5-23.

Calzada-Nova G, Schnitzlein W, Husmann R, Zuckermann FA. 2010. Characterization of the cytokine and maturation responses of pure populations of porcine plasmacytoid dendritic cells to porcine viruses and toll-like receptor agonists. Veterinary Immunology and Immunopathology 135: 20-33.

Cobbold C, Windsor M, Wileman T. 2001. A virally encoded chaperone specialized for folding of the major capsid protein of African swine fever virus. Journal of Virology 75: 7221-29.

King DP, Reid SM, Hutchings GH, Grierson SS, Wilkinson PJ, et al. 2003. Development of a TaqMan (R) PCR assay with internal amplification control for the detection of African swine fever virus. Journal of Virological Methods 107: 53-61.

King K, Chapman D, Argilaguet JM, Fishbourne E, Hutet E, et al. 2011. Protection of European domestic pigs from virulent African isolates of African swine fever virus by experimental immunisation. Vaccine 29: 4593-600.

Shibata Y, Berclaz PY, Chroneos ZC, Yoshida M, Whitsett JA, Trapnell BC. 2001. GM-CSF regulates alveolar macrophage differentiation and innate immunity in the lung through PU.1. Immunity 15: 557-67.

Sanchez EG, Riera E, Nogal M, Gallardo C, Fernandez P, et al. 2017. Phenotyping and susceptibility of established porcine cells lines to African Swine Fever Virus infection and viral production. Sci Rep 7: 10369.

Abrams CC, Goatley L, Fishbourne E, Chapman D, Cooke L, et al. 2013. Deletion of virulence associated genes from attenuated African swine fever virus isolate Our T88/3 decreases its ability to protect against challenge with virulent virus. Virology 443: 99-105.

Sanchez-Cordon PJ, Chapman D, Jabbar T, Reis AL, Goatley L, et al. 2017. Different routes and doses influence protection in pigs immunised with the naturally attenuated African swine fever virus isolate OURT88/3. Antiviral Research 138: 1-8.

Boinas FS, Hutchings GH, Dixon LK, Wilkinson PJ. 2004. Characterization of pathogenic and non-pathogenic African swine fever virus isolates from Ornithodoros erraticus inhabiting pig premises in Portugal. Journal of General Virology 85: 2177-87.

Reis AL, Abrams CC, Goatley LC, Netherton C, Chapman DG, et al. 2016. Deletion of African swine fever virus interferon inhibitors from the genome of a virulent isolate reduces virulence in domestic pigs and induces a protective response. Vaccine 34: 4698-705.

Vietnamese Substantive Exam, Notification No. 1381/SHTT-SC.IP; Intellectual Property Office of Vietnam; Vietnamese Appl. No. 1-2022-00360, dated Jan. 15, 2025; 4 pages.

Malaysian Substantive Examination Adverse Report; Intellectual Property Corporation of Malaysia; Malaysian Appl. No. PI2022000031; dated Sep. 20, 2024; 5 pages.

Japanese Office Action, Japan Patent Office; JP Application No. 2022-500830; Mar. 28, 25; 8 pages.

Adams Dolph O., Macrophages, in: Cell Culture. Methods in Enzymology, vol. 58., W .- B. Jacoby and I. H. Pastan editors, Academic Press, San Diego, CA. 1979, pp. 494-506.

Davies, John Q. et al., Isolation and Culture of Human Macrophages, Chapter 8, in: Basic Cell Culture Protocols, Helgason C.D. and Miller C.L., editors, Humana Press, Inc. New Jersey, 2005, pp. 105-116.

Gao, Qi et al., "Adaptation of African swine fever virus to porcine kidney cells stably expressing CD163 and Siglec1," Front Immunol., Oct. 27, 2022;13: 1015224.

Meloni, Dionigia et al., "Cell Lines for the Development of African Swine Fever Virus Vaccine Candidates: An Update." Vaccines, 2022, 10, 707, MDPI, pp. 1-25.

Wang, Tao et al., "Adaptation of African swine fever virus to HEK293T cells," Transboundary and Emerging Diseases, Jul. 27, 2021; pp. 2853-2866.

Weingartl, H.M. et al., "Continuous porcine cell lines developed from alveolar macrophages: partial characterization and virus susceptibility," Journal of Virological Methods, Jul. 2002; 104; pp. 203-216.

* cited by examiner

Georgia 2007 progeny titre

Haemorrhagic gastro-hepatic lymph node (A) of control pig (#19) and enlarged spleen (31 cm long) (B) of control pig (#21) after challenged with ASFV OURT88/1. OURT88/3 ZMAC prepared ASFV immunised pigs shows no sign of haemorrhage in gastro-heptic lymph (C) (pig #11) nor enlargement of spleen (D: 21 cm long) (pig #12) after challenged with OURT88/1 ASFV.

METHODS FOR GROWING AFRICAN SWINE FEVER VIRUS IN FETAL PORCINE LUNG ALVEOLAR MACROPHAGE CELLS

CROSS REFERENCE TO RELATED APPLICATIONS

This application is a U.S. National Phase of International PCT Application No. PCT/US2020/041762 filed on Jul. 13, 2020, which claims priority to U.S. Provisional Patent Application Ser. No. 62/873,075 filed on Jul. 11, 2019 and U.S. Provisional Patent Application Ser. No. 62/952,889 filed on Dec. 23, 2019, the contents of each application are incorporated by reference herein in their entirety.

STATEMENT ON FEDERALLY SPONSORED RESEARCH OR DEVELOPMENT

Not Applicable.

BACKGROUND

African Swine Fever (ASF) is a highly contagious hemorrhagic viral disease of domestic and wild pigs, which is responsible for serious economic and production losses. ASF is also a transboundary animal disease. Transboundary animal diseases are highly contagious epidemic diseases that can spread rapidly irrespective of national borders. Such diseases cause high rates of death and disease in animals, thereby, having serious socio-economic and sometimes public health consequences while constituting a constant threat to the livelihoods of livestock farmers. In the event of an outbreak of ASF, there is the potential for high rates of death and disease in swine such that the quantity and quality of meat from swine could be significantly reduced. A major limitation to controlling ASF disease is the lack of available and effective cells and methods for experimenting with ASF virus and vaccine and diagnostic technologies capable of addressing ASF disease.

SUMMARY

According to an embodiment, a method for generating progeny of an African swine fever (ASF) virus may include providing an isolated or purified fetal porcine lung alveolar macrophage cell capable of replicating the ASF virus, wherein the cell may be cultured for at least 5 passages; exposing the cell to the ASF virus; and allowing the ASF virus to replicate in the cell; thereby generating progeny of the ASF virus.

In some embodiments, the cell may be a ZMAC cell or a derivative thereof.

In some embodiments, the cell may be selected from the group consisting of ZMAC-1, ZMAC-4, a cell of a deposit with the American Type Culture Collection designated as ATCC Patent Deposit No. PTA-8764, and a derivative of any of the foregoing.

In some embodiments, the method may further include contacting the cell with a growth factor composition.

In some embodiments, the growth factor composition may include macrophage colony stimulating factor (MCSF) or granulocyte-macrophage colony stimulating factor (GMCSF).

In some embodiments, the cell may be obtained from a porcine fetal subject from about 30 to about 90 days of gestational age.

In some embodiments, the cell may be cultured for at least 10 passages.

In some embodiments, the cell may be cultured for at least 20 passages.

According to another embodiment, a method for producing an ASF vaccine may include providing a modified-live virus (MLV) strain of ASF virus; and growing the MLV strain in an isolated or purified fetal porcine lung alveolar macrophage cell capable of replicating the ASF MLV strain.

In some embodiments, the cell may be a primary cell, cell population, cell line, or variant or derivative thereof.

In some embodiments, the cell may be a ZMAC cell or a derivative thereof.

In some embodiments, the cell may be selected from the group consisting of ZMAC-1, ZMAC-4, a cell of a deposit with the American Type Culture Collection designated as ATCC Patent Deposit No. PTA-8764, and a derivative of any of the foregoing.

In some embodiments, the method may further include contacting the cell with a growth factor composition.

In some embodiments, the growth factor composition may include macrophage colony stimulating factor (MCSF) or granulocyte-macrophage colony stimulating factor (GMCSF).

In some embodiments, the cell may be obtained from a porcine fetal subject from about 30 to about 90 days of gestational age.

In some embodiments, the cell may be a cell line.

According to another embodiment, a method for growing an ASF virus may include isolating a fetal porcine lung alveolar macrophage cell from a porcine fetal lung including providing a porcine fetal subject, obtaining a cell-containing bronchoalveolar lavage sample from the subject, and separating the macrophage cell from the sample; culturing the cell; and contacting the cell with the ASF virus so as to allow viral replication; thereby growing the ASF virus.

In some embodiments, the culturing may include passaging the cell for at least 5 passages or growing the cell for at least 10 days of continuous culture or a combination thereof.

In some embodiments, the culturing may include contacting the cell with a growth factor composition.

In some embodiments, the growth factor composition may include macrophage colony stimulating factor (MCSF) or granulocyte-macrophage colony stimulating factor (GMCSF).

In some embodiments, the cell may be obtained from a porcine fetal subject from about 30 to about 90 days of gestational age.

In some embodiments, the culturing may include passaging the cell for at least 20 passages.

According to another embodiment, a method for detecting the presence of an ASF virus in a porcine subject may include providing an isolated or purified fetal porcine lung alveolar macrophage cell capable of replicating the ASF virus, wherein the cell may be cultured for at least 5 passages; contacting the cell with a sample; incubating the cell under suitable conditions; and detecting the presence of the ASF virus in the cell.

In some embodiments, the cell may be a ZMAC cell or a derivative thereof.

In some embodiments, the cell may be selected from the group consisting of ZMAC-1, ZMAC-4, a cell of a deposit with the American Type Culture Collection designated as ATCC Patent Deposit No. PTA-8764, and a derivative of any of the foregoing.

In some embodiments, the method may further include contacting the cell with a growth factor composition.

3

In some embodiments, the growth factor composition may include macrophage colony stimulating factor (MCSF) or granulocyte-macrophage colony stimulating factor (GMCSF).

In some embodiments, the cell may be obtained from a porcine fetal subject from about 30 to about 90 days of gestational age.

In some embodiments, the sample may be selected from the group consisting of blood, serum, plasma, lymph, saliva, nasal secretions, feces, urine, semen, sputum, cerebrospinal fluid, tears, mucus, sweat, milk, and tissue cells.

In some embodiments, the tissues cells may be selected from the group consisting of thymus, lymph node, spleen, bone marrow, and tonsil.

In some embodiments, the detecting may include utilizing a hemadsorption assay or immunofluorescence.

According to another embodiment, a vaccine may include the progeny of an ASF virus of the present disclosure in a carrier.

In some embodiments, the vaccine may further include an adjuvant.

According to another embodiment, a method of eliciting an immune response against ASFV in a porcine may include administering an effective amount of the vaccine of the present disclosure to the porcine.

In some embodiments, the route of administration may be selected from the group consisting of parenterally, orally, intranasally, and mucosally.

This summary is not intended to identify key or essential features of the claimed subject matter, nor is it intended to be used as an aid in limiting the scope of the claimed subject matter. Further embodiments, forms, features, and aspects of the present disclosure shall become apparent from the description and figures provided herewith.

BRIEF DESCRIPTION OF THE DRAWINGS

The teachings of some embodiments of the present disclosure will be better understood by reference to the description taken in conjunction with the accompanying drawings, wherein.

4

Figure 10:
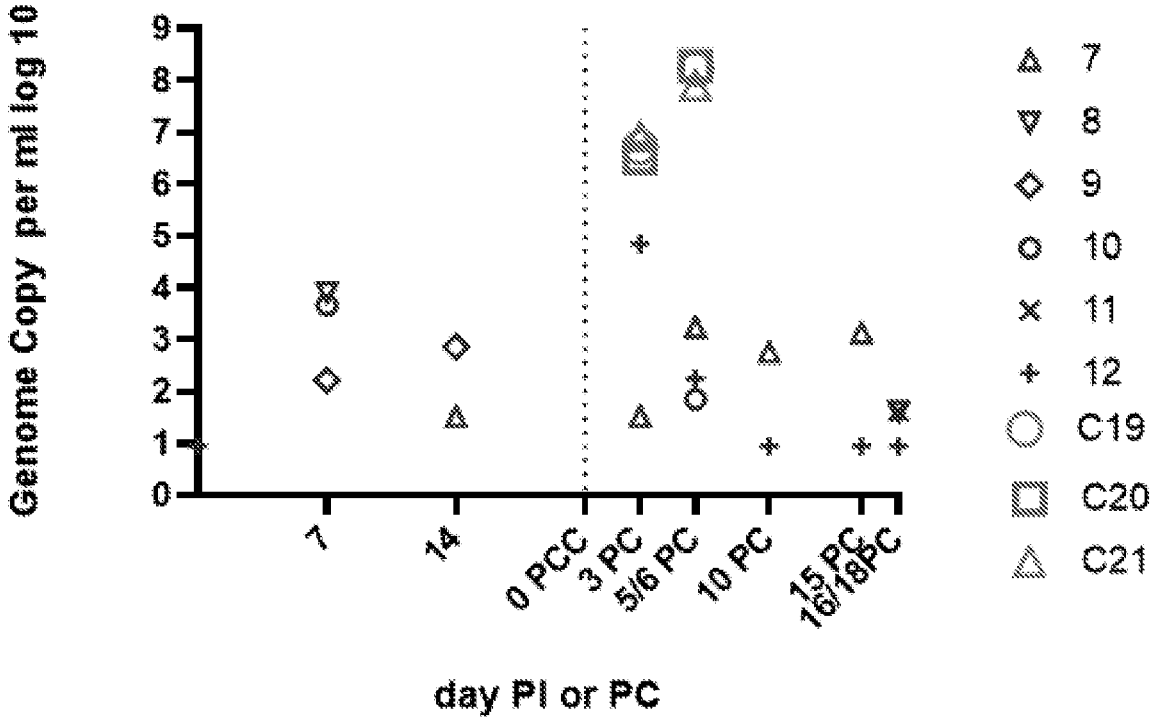
Figure 11:
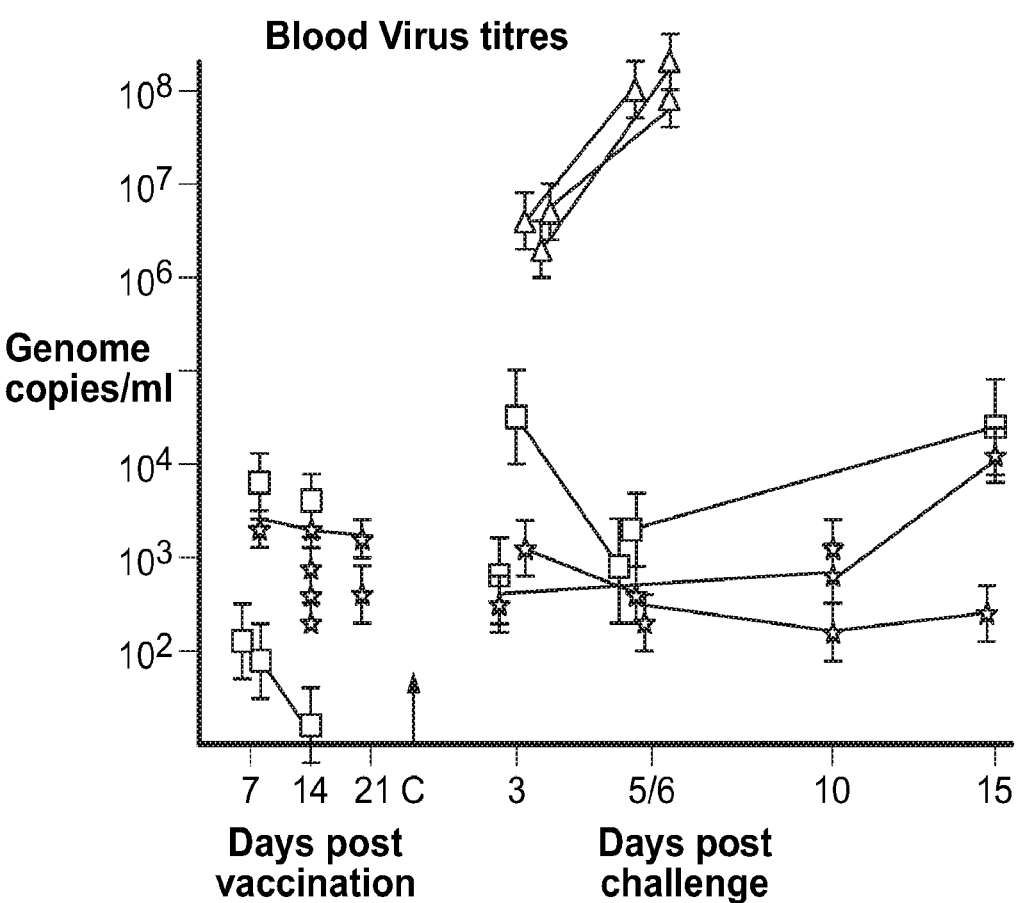

FIG. 10 shows levels of virus genome per ml blood following immunization of pigs with OURT88/3 passaged in ZMAC-4 cells according to an embodiment; and FIG. 11 shows titers of ASFV genome copies in infected blood estimated by quantitative PCR according to an embodiment.

DETAILED DESCRIPTION

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "some embodiments," "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

The present disclosure provides a method for generating progeny of an African swine fever (ASF) virus. In some embodiments, the method may include providing an isolated or purified fetal porcine lung alveolar macrophage cell capable of replicating the ASF virus, wherein the cell may be cultured for at least 5 passages; exposing the cell to the ASF virus; and allowing the ASF virus to replicate in the cell; thereby generating progeny of the ASF virus.

African swine fever also may be referred to herein as ASF. African swine fever virus also may be referred to herein as ASFV. In some embodiments, exposing a cell to ASFV may refer to infecting the cell with ASFV.

As used herein, the term "porcine" refers to any animal, wild or domestic, that is a member of the biological family Suidae, including without limitation *Babyrousa babyrussa* or Golden *Babirusa, Babyrousa celebensis* or *Sulawesi Babirusa, Babyrousa togeanensis* or *Togian Babirusa, Hylochoerus meinertzhageni* or Giant Forest Hog, *Phacochoerus aethiopicus* or Cape, Somali or Desert Warthog, *Phacochoerus africanus* or Common Warthog, *Porcula salvania* or Pygmy Hog, *Potamochoerus larvatus* or Bushpig, *Potamochoerus porcus* or Red River Hog, *Sus ahoenobarbus* or Palawan Bearded Pig, *Sus barbatus* or Bearded Pig, *Sus bucculentus* or Vietnamese Warty Pig, *Sus cebifrons* or Visayan Warty Pig, *Sus celebensis* or Celebes Warty Pig, *Sus heureni* or Flores Warty Pig, *Sus oliveri* or Mindoro Warty Pig, *Sus philippensis* or Philippine Warty Pig, *Sus scrofa* or Wild Boar or Domestic Pig, *Sus verrucosus* or Javan Warty Pig, and any other boar, sow, piglet, farrow, shoat, gilt, barrow, hog, swine, or *sus* of either sex or any age.

As used herein, the term "cell" may refer to a biological entity as would be understood in the art and which is intended to encompass specific entities that may be described as a primary cell or a cell line. When several of these terms are used herein, it will be appreciated that such usage is merely for purposes of emphasizing well understood distinctions. For example, the phrase "a cell or cell line" may emphasize the contrast between an original primary isolate versus an immortalized version which could be a direct derivative of the original primary isolate. In some embodiments, a cell or cell line of the present disclosure may be one or more of a spontaneous immortalized variant, deliberately transformed derivative, other variant or derivative, and an otherwise immortalized version of a primary cell or cell line as described herein.

In some embodiments, a cell line of the present disclosure may be a porcine lung alveolar macrophage cell line which may be capable of supporting the growth of ASF. In some embodiments, a cell of the present disclosure may be obtained from porcine fetal lung samples. In some embodiments, a cell of the present disclosure may be a fetal porcine lung alveolar macrophage cell. In some embodiments, a cell of the present disclosure may be a ZMAC cell. ZMAC cells may be characterized and/or may be observed to have the capability of supporting ASFV infectivity and growth. In some embodiments, a cell of the present disclosure may be designated as ZMAC-1. In some embodiments, a cell of the present disclosure may be designated as a deposit with the American Type Culture Collection designated as ATCC Patent Deposit No. PTA-8764 or derived therefrom. As used herein, the term "ATCC" may refer to American Type Culture Collection. In some embodiments, a cell of the present disclosure may be designated as ZMAC1107-4. ZMAC1107-4 may also be referred to herein as ZMAC-4, and such terms are used interchangeably herein. In some embodiments, a cell of the present disclosure may include any cell, or have the features of any cell, described in U.S. Pat. Nos. 8,202,717, 8,663,984, and 9,169,465, each of which is incorporated by reference herein in their entireties. In the event of any inconsistency between these prior patents and the present disclosure, the present disclosure shall take precedence.

In embodiments including a cell of the present disclosure that is obtained from porcine fetal lung samples, the porcine fetal lung may be from a porcine fetus having a gestational age from about 20 to about 80 days. In some embodiments, the porcine fetal lung may be from a porcine fetus having a gestational age from about 50 to about 70 days. In some embodiments, the porcine fetal lung may be from a porcine fetus having a gestational age from about 30 to about 90 days. It should be appreciated that porcine fetuses having other gestational ages are contemplated to be within the scope of the present disclosure.

As used herein, the terms "isolating," "isolate," "isolated," and the like may refer to a manipulated state that is different than that which is the natural state and/or is modified relative to a starting material, in which case the term is meant to be consistent with the concept of being purified. For example, an isolated primary cell is excised from a natural tissue or other source in a host organism and maintained apart from the original source. As another example, a cell component may be placed in culture or further separated from a lung lavage fluid-based sample, thus, achieving a relatively isolated cell.

As used herein, the term "purified" may refer to a condition wherein there has been a relative enrichment, separation, and/or removal of a substance relative to a starting material. The term may encompass conditions of an at least partial purification and does not necessarily imply an absolute state of purity. For example, the term may apply to a cell that is capable of reproducing an ASF virus and present in a mixed culture and independently can be applicable to what may customarily be considered a pure culture. The term may apply to a primary cell culture which is optionally a mixed culture. The term may apply to a cell line.

As used herein, the term "culture," "cultured," "culturing," and like terms refer to the process by which cells are grown under controlled conditions and generally outside their natural environment. In some embodiments, the cells may first be removed from a porcine and subsequently grown in a favorable artificial environment. In some embodiments, the cells may be removed directly from tissue and disaggregated by enzymatic or mechanical means before cultivation. In some embodiments, the cells may be derived from a cell line or cell strain that has already been established.

As used herein, the term "passage," "passages," "passaged," "passaging," and like terms refer to subculturing cells, which may include the removal of the medium and transfer of cells from a previous culture into fresh growth medium, thereby, enabling the further propagation of the cells. In some embodiments, a cell of the present disclosure may be cultured for at least 5 passages. In some embodiments, a cell of the present disclosure may be cultured for at least 10 passages. In some embodiments, a cell of the present disclosure may be cultured for at least 15 passages. In some embodiments, a cell of the present disclosure may be cultured for at least 20 passages. In some embodiments, a cell of the present disclosure may be cultured for at least 50 passages. In some embodiments, culturing may include passaging a cell of the present disclosure for at least 5 passages and/or growing a cell of the present disclosure for at least 10 days of continuous culturing. It should be appreciated that the present disclosure contemplates culturing a cell of the present disclosure for other passaging intervals.

A method of the present disclosure may further include contacting a cell of the present disclosure with a growth factor composition. In some embodiments, the growth factor composition may include macrophage colony stimulating factor (MCSF). In some embodiments, the growth factor composition may include granulocyte-macrophage colony stimulating factor (GMCSF).

The present disclosure also provides a method for producing an ASF vaccine. In some embodiments, the method may include providing a modified-live virus (MLV) strain of ASF virus, and growing the MLV strain in an isolated or purified fetal porcine lung alveolar macrophage cell capable of replicating the ASF MLV strain.

The ASFV virus used in the methods and compositions of the present disclosure may be live, attenuated, or inactivated. As used herein the terms "attenuated," "modified-live virus," "MLV," and the like may refer to an amount of ASFV that has been altered such that it is no longer capable of causing ASF but is still capable of infection and replicating in a cell of the present disclosure. As used herein, the terms "inactivated," "killed," "dead," and like terms may refer to a killed ASFV. As used herein, the term "vaccine" may refer to an MLV strain of ASFV or a killed ASFV, or a portion of ASFV's structure, that upon administration stimulates antibody production against the ASFV but is incapable of causing severe infection.

The present disclosure also provides a method for growing an ASF virus. The method may include isolating a fetal porcine lung alveolar macrophage cell from a porcine fetal lung comprising providing a porcine fetal subject, obtaining a cell-containing bronchoalveolar lavage sample from the subject, and separating the macrophage cell from the sample; culturing the cell; and contacting the cell with the ASF virus so as to allow viral replication; thereby growing the virus.

The present disclosure also provides a method for detecting the presence of an ASF virus in a porcine subject. In some embodiments, the method may include providing an isolated or purified fetal porcine lung alveolar macrophage cell capable of replicating the ASF virus, wherein the cell is cultured for at least 5 passages; contacting the cell with a sample; incubating the cell under suitable conditions; and detecting the presence of the ASF virus in the cell. Such a detection method may be used to diagnose ASF.

As used herein, the term "sample" may refer to blood, serum, plasma, lymph, saliva, nasal secretions, tissue cells, serum, saliva, semen, sputum, cerebrospinal fluid (CSF), tears, mucus, sweat, milk, or brain extracts. The bodily tissue may include thymus, lymph node, spleen, bone marrow, or tonsil tissue.

As used herein, the term "suitable conditions," in the context of incubating a cell of the present disclosure, may refer to adequate conditions of temperature, humidity, gas mixtures in the environment, and the like. In some embodiments, the temperature may be 37° C. (i.e., degrees Celsius).

In some embodiments, detecting the presence of an ASF virus may include utilizing a hemadsorption assay or immunofluorescence. It should be appreciated that the present disclosure contemplates other techniques that may be used to detect the presence of ASF virus.

The present disclosure also provides a vaccine comprising progeny of an ASF virus in a carrier. Vaccines may function by preparing the immune system of a porcine subject to mount a response to ASFV. In an embodiment, a vaccine may include an antigen, which may be a progeny of an ASFV of the present disclosure, or a portion thereof, that may be introduced into the body of a porcine subject to be vaccinated in a non-toxic, non-infectious, and/or non-pathogenic form. The ASFV antigen in a vaccine of the present disclosure may cause the porcine subject's immune system to be "primed" or "sensitized" to the ASFV from which the antigen is derived. Subsequent exposure of the immune system of the porcine subject to the ASFV may result in a rapid and robust specific immune response that may control or destroy the ASFV before it can multiply and infect or damage enough cells in the host porcine subject to cause disease symptoms.

In an embodiment, it may be necessary to enhance the immune response to the antigens present in a vaccine in order to stimulate the immune system to a sufficient extent to make a vaccine effective, that is, to confer immunity. To this end, additives known as adjuvants (or immune potentiators) have been devised which may enhance the in vivo immune response to an antigen in a vaccine composition. In some embodiments, a vaccine of the present disclosure may further include an adjuvant.

The adjuvant may be any composition, pharmacological, or immunological agent that modifies the effect of other agents, such as the antigen described herein. Examples of adjuvants may include, but are not limited to *Mycobacterium lysate* (including a *Mycobacterium tuberculosis* whole cell lysate), a *Mycobacterium smegmatis* (including *Mycobacterium smegmatis* whole cell lysate), choleratoxin B subunit, and *E. coli* heat labile mutant toxin. Other examples of adjuvants may include evolutionarily conserved molecules, so called PAMPs, which may include liposomes, lipopolysaccharide (LPS), molecular cages for antigen, components of bacterial cell walls, and endocytosed nucleic acids such as double-stranded RNA (dsRNA), single-stranded DNA (ssDNA), and unmethylated CpG dinucleotide-containing DNA.

Additional examples of adjuvants may include, but are not limited to, aluminum containing adjuvants that may include suspensions of minerals (or mineral salts, such as aluminum hydroxide, aluminum phosphate, aluminum hydroxyphosphate) onto which antigen may be adsorbed. Additional examples of adjuvants may include, but are not limited to, aluminum-(alum-) free adjuvants, which may be formulated in the absence of any such aluminum salts. Alum-free adjuvants may include oil and water emulsions, such as water-in-oil, water-oil-water, and oil-in-water (and variants thereof, including double emulsions and reversible emulsions), liposaccharides, lipopolysaccharides, immuno-stimulatory nucleic acids (such as CpG oligonucleotides), liposomes, Toll-like Receptor agonists (particularly, TLR2, TLR4, TLR7/8 and TLR9 agonists), and various combinations of such components.

A non-limiting list of carriers that may be utilized in the vaccine of the present disclosure may include without limitation water or saline, gel, salve, solvent, oil, diluent, fluid ointment base, liposome, micelle, giant micelle, synthetic polymer, emulsion, a solid particle made of lipid, and the like. It should be appreciated that any diluent known in the art may be utilized in accordance with the present disclosure. In some embodiments of the present disclosure, the diluent may be water soluble. In some embodiments of the present disclosure, the diluent may be water insoluble. As used herein, the term "diluent" may include without limitation water, saline, phosphate buffered saline (PBS), dextrose, glycerol, ethanol, buffered sodium or ammonium acetate solution, or the like and combinations thereof.

The present disclosure also provides a method of eliciting an immune response against ASFV in a porcine. In some embodiments, the method may comprise administering an effective amount of a vaccine of the present disclosure to a porcine. The immune response may be protective for the porcine.

In carrying out the methods of the present disclosure, an effective amount of vaccine is administered to a porcine. As used herein, the term "effective amount," in the context of administration, refers to the amount of vaccine that when administered to a pig is sufficient to produce an immune response to ASFV. Such an amount should result in no or few adverse events in the porcine. Similarly, such an amount should result in no or few toxic effects. It should be appreciated that the amount of vaccine may vary depending upon a number of factors, including without limitation the type of porcine treated, the porcine's age, size, weight, and general physical condition, and the dosing regimen.

As used herein, an "immune response" may be a response of a cell of the immune system, such as a B cell, T cell, or monocyte, to a stimulus. An immune response may be a B cell response, which results in the production of specific antibodies, such as antigen specific neutralizing antibodies. An immune response may also be a T cell response, such as a CD4+ response or a CD8+ response. In some embodiments, the response may specific for a particular antigen (that is, an "antigen-specific response"). An immune response may also include the innate response. If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo.

It should be appreciated that the vaccine utilized in the methods of the present disclosure may be administered using a variety of applicable routes, including, without limitation, oral, intravenous ("IV"), subcutaneous ("SC"), intramuscular ("IM"), intraperitoneal, intradermal, intraocular, intrapulmonary, intranasal, transdermal, subdermal, topical, mucosal, nasal, impression into skin, intravaginal, intrauterine, intracervical, and rectal. In some embodiments of the present disclosure, the intranasal route of administration may include intranasal drops. In some embodiments of the present disclosure, the intranasal route of administration may include intranasal aerosol delivery. In some embodiments of the present disclosure, intranasal aerosol delivery may include nasal spray delivery.

The present disclosure addresses the problems of ASF disease by providing the cells and methods of the present disclosure. The main target cells for ASFV replication in vivo are monocytes and macrophages. The lack of porcine macrophage cell lines resembling the in vivo target cells for ASFV replication has restricted research on the virus host interaction, limited the development of live-attenuated vaccines, and made virus diagnosis more cumbersome. The use of established cell lines derived from the kidney of African green monkeys, such as Vero and COS-1, have enabled the amplification of ASFV for research purposes. However, their use requires that the virus first be adapted to grow in that type of cell line, restricting its use to a limited number of laboratory strains that must have gone through a prolonged adaptation process to efficiently grow in cell culture. Since wild-type ASFV isolates from natural outbreaks have been found not to replicate in these conventional simian-derived established cell cultures, swine monocytes and macrophages are the in vitro system of choice to grow virus stocks and to mimic natural ASFV infections. Although this may be adequate for research purposes, it is not adequate for the development of commercial vaccines, since the use of primary cells are not suitable for regulatory approval by the USDA Center for Veterinary Biologics (CVB), as a cell substrate to produce fully licensed commercial vaccines. Attempts have been made to use established cell lines to develop attenuated strains of ASFV. Unfortunately, serial passage of the Georgia 2007 wild-type strain of ASFV for 110 times in Vero cells for the purpose of developing an attenuated vaccine strain resulted in virus attenuation but also resulted in the loss of vaccine efficacy. Consequently, culture of field isolates and even recently developed Georgia 2007 gene deleted ASFV vaccine candidates are being performed in primary cultures of porcine macrophages derived from either peripheral blood or bone-marrow. In contrast, as shown in in the present disclosure, the wild-type ASFV strain Georgia 2007/1 as well as several other wild-type and attenuated strains of ASFV are able to readily and efficiently replicate in the ZMAC cell. Moreover, as shown in the present disclosure, twelve passages of the attenuated strain of ASFV OURT88/3 in ZMAC cells did not reduce its ability to induce protective immunity in swine against challenge with virulent virus.

The presence of specific receptors necessary for virus infection are expressed on the host cell membrane and, thus, constitute a determinant for viral tropism and internalization. It has been reported that monocytes/macrophages with a higher maturation and differentiation state are the cell subset preferentially infected by ASFV. In this respect, it has been described that the higher percentage of mature monocytes/macrophages being infected with wild-type ASFV correlates with a higher expression of CD163 and SWC9/CD203a. Although cell surface expression of CD163 was initially considered to be necessary for cells to become infected with ASFV, subsequent investigations contradicted this observation, by showing that CD163 negative monocytes could be infected by ASFV. Moreover, gene-edited pigs lacking CD163, as well as monocytes and macrophages derived from them, were fully susceptible to infection with the wild-type Georgia 2007/1 strain of ASFV. Thus, CD163 does not appear to be required for ASFV infection. In the case of SWC9/CD203a, up-regulation of the expression of this molecule by monocytes and macrophages is associated with their differentiation and maturation into macrophages. Monocytes do not express SWC9/CD203a and are primarily resistant to ASFV infection. As these cells differentiate towards a mature macrophage they up-regulate the expression of SWC9/CD23a and become susceptible to ASFV infection. As shown in the present disclosure, ZMAC cells do not express SWC9/CD203a, and thus can be considered an immature type of macrophage. Thus, the ability of the ZMAC cells to efficiently replicate wild-type strains of ASFV was unexpected since the cells appear to be immature macrophages and do not express a cell surface molecule (SWC9/CD203a) that has been associated with susceptibility to infection by ASFV. In addition, the ability of ZMAC cells to efficiently replicate wild-type ASFV is unprecedented, as the porcine alveolar macrophage cell lines 3D4/2, 3D4/21 and 3D4/3, described by Weingartl et al. (Weingartl HM4, Sabara M, Pasick J, van Moorlehem E, Babiuk L). Continuous porcine cell lines developed from alveolar macrophages: partial characterization and virus susceptibility. *J Virol Methods*. 2002; 104(2):203-216. Doi: 10.1016/s0166-0934(02)00085-x), were inefficiently infected by wild-type ASFV, and did not support the successive passage of ASFV. As described in the present disclosure, ZMAC cells efficiently enabled growth of the wild-type ASFV strain Georgia 2007/1, yielding high titers.

In addition to the aspects and embodiments described and provided elsewhere in the present disclosure, the following non-limiting list of embodiments are also contemplated.

1. A method of generating progeny of an African swine fever (ASF) virus comprising:

providing an isolated or purified fetal porcine lung alveolar macrophage cell capable of replicating the ASF virus, wherein the cell is cultured for at least 5 passages;

exposing the cell to the ASF virus; and allowing the ASF virus to replicate in the cell;

thereby generating progeny of the ASF virus.

2. The method of clause 1, wherein the cell is selected from the group consisting of ZMAC, a deposit with the American Type Culture Collection designated as ATCC Patent Deposit No. PTA-8764, and a derivative of any of the foregoing.

3. The method of clause 1, wherein the cell is selected from the group consisting of ZMAC-1, ZMAC-4, a cell of a deposit with the American Type Culture Collection designated as ATCC Patent Deposit No. PTA-8764, and a derivative of any of the foregoing.

4. The method of clause 1, further comprising contacting the cell with a growth factor composition.

5. The method of clause 4, wherein the growth factor composition comprises macrophage colony stimulating factor (MCSF) or granulocyte-macrophage colony stimulating factor (GMCSF).

6. The method of clause 1, wherein the cell is obtained from a porcine fetal subject from about 30 to about 90 days of gestational age.

7. A method of producing an ASF vaccine, comprising: providing a modified-live virus (MLV) strain of ASF virus, and growing the MLV strain in an isolated or purified fetal porcine lung alveolar macrophage cell capable of replicating the ASF MLV strain.

8. The method of clause 7, wherein the cell is a primary cell, cell population, cell line, or variant or derivative thereof.

9. The method of clause 7, wherein the cell is selected from the group consisting of ZMAC, a deposit with the American Type Culture Collection designated as ATCC Patent Deposit No. PTA-8764, and a derivative of any of the foregoing.

10. The method of clause 7, wherein the cell is selected from the group consisting of ZMAC-1, ZMAC-4, a cell of a deposit with the American Type Culture Collection designated as ATCC Patent Deposit No. PTA-8764, and a derivative of any of the foregoing.

11. The method of clause 7, further comprising contacting the cell with a growth factor composition.

12. The method of clause 11, wherein the growth factor composition comprises macrophage colony stimulating factor (MCSF) or granulocyte-macrophage colony stimulating factor (GMCSF).

13. The method of clause 7, wherein the cell is obtained from a porcine fetal subject from about 30 to about 90 days of gestational age.

14 A method of growing an ASF virus, comprising:
isolating a fetal porcine lung alveolar macrophage cell from a porcine fetal lung by steps comprising providing a porcine fetal subject, obtaining a cell-containing bronchoalveolar lavage sample from the subject, and separating the macrophage cell from the sample;
culturing the cell; and
contacting the cell with the ASF virus so as to allow viral replication;
thereby growing the virus.

15. The method of clause 14, wherein the culturing comprises passaging the cell for at least 5 passages and/or growing the cell for at least 10 days of continuous culture.

16. The method of clause 14, wherein the culturing comprises contacting the cell with a growth factor composition.

17. The method of clause 16, wherein the growth factor composition comprises macrophage colony stimulating factor (MCSF) or granulocyte-macrophage colony stimulating factor (GMCSF).

18. The method of clause 14, wherein the cell is obtained from a porcine fetal subject from about 30 to about 90 days of gestational age.

19. The method of clause 1, wherein the cell is cultured for at least 10 passages.

20. The method of clause 1, wherein the cell is cultured for at least 20 passages.

21. The method of clause 1, wherein the cell is a cell line.

22. The method of clause 7, wherein the cell is a cell line.

23. The method of clause 14, wherein the culturing comprises passaging the cell for at least 20 passages.

24. An isolated fetal porcine lung alveolar macrophage cell, wherein the cell is capable of infection by and/or reproducing the ASF virus, and wherein the cell is cultured for at least 5 passages.

25. The cell of clause 24, wherein the cell is propagated in culture for at least 10 passages.

26. The cell of clause 24, wherein the cell is propagated in culture for at least 20 passages.

27. The cell of clause 24, wherein the cell is propagated in culture for at least 50 passages.

28. The cell of clause 24, wherein the cell is capable of growing ASF virus at a titer of at least $10^4$ TCID50/ml.

29. The cell of clause 24, wherein the cell is capable of growing ASF virus at a titer of at least about $3.16 \times 10^5$ TCID50/ml.

30. The cell of clause 24, wherein the cell is capable of growing ASF virus at a titer of at least about $3.16 \times 10^6$ TCID50/ml.

31. The cell of clause 24, wherein the cell is capable of growing ASF virus at a titer of at least about $3.16 \times 10^7$ TCID50/ml.

32. The cell of clause 24, wherein the cell is capable of growing ASF virus at a titer of at least about $6.81 \times 10^7$ TCID50/ml.

33. The cell of clause 24, wherein the cell is from a porcine fetus of about 30 to about 90 days of gestational age.

34. A fetal porcine lung alveolar macrophage cell line, wherein the cell line is capable of infection by and/or reproducing the ASF virus.

35. The cell of clause 34, wherein the cell is capable of growing ASF virus at a titer of at least $10^4$ TCID50/ml.

36. The cell of clause 34, wherein the cell is capable of growing ASF virus at a titer of at least about $3.16 \times 10^5$ TCID50/ml.

37. The cell of clause 34, wherein the cell is capable of growing ASF virus at a titer of at least about $3.16 \times 10^6$ TCID50/ml.

38. The cell of clause 34, wherein the cell is capable of growing ASF virus at a titer of at least about $3.16 \times 10^7$ TCID50/ml.

39. The cell of clause 34, wherein the cell is capable of growing ASF virus at a titer of at least about $6.81 \times 10^7$ TCID50/ml.

40. The cell line of clause 34, wherein the cell line is from a cell of a porcine fetus of about 30 to about 90 days of gestational age.

41. An isolated ZMAC-1 cell represented by a deposit with the American Type Culture Collection designated as ATCC Patent Deposit No. PTA-8764 or derived therefrom.

42. The cell of clause 41, wherein the cell is capable of growing ASF virus at a titer of at least $10^4$ TCID50/ml.

43. The cell of clause 41, wherein the cell is capable of growing ASF virus at a titer of at least about $3.16 \times 10^5$ TCID50/ml.

44. The cell of clause 41, wherein the cell is capable of growing ASF virus at a titer of at least about $3.16 \times 10^6$ TCID50/ml.

45. The cell of clause 41, wherein the cell is capable of growing ASF virus at a titer of at least about $3.16 \times 10^7$ TCID50/ml.

46. The cell of clause 41, wherein the cell is capable of growing ASF virus at a titer of at least about $6.81 \times 10^7$ TCID50/ml.

47. A method of isolating a cell from a porcine fetal lung, comprising the steps of:
providing a porcine fetal subject;
obtaining a cell-containing sample from the subject;
separating a cell from the sample, and culturing the cell for at least 5 passages, wherein the cell is capable of replicating ASF virus;
thereby isolating the cell.

48. A method of isolating a cell from a porcine fetal lung, comprising the steps of:

providing a porcine fetal subject;

obtaining a cell containing sample from the subject, wherein the cell-containing sample is a bronchoalveolar lavage sample; and separating a cell from the sample, wherein the cell is capable of replicating ASF virus; thereby isolating the cell.

49. The method of clause 47, wherein the separating step is by density gradient centrifugation.

50. The method of clause 47, wherein the cell is a macrophage.

51. The method of clause 47, further comprising growing the cell for at least 10 days in continuous culture.

52. The method of clause 47, wherein the culturing is for at least 10, 20, or 50 passages.

53. The method of clause 47, wherein the porcine fetal subject is from about 30 to about 90 days of gestational age.

54. A method of isolating a cell from a porcine fetal lung, comprising the steps of providing a porcine fetal subject a cell-containing sample from the subject, separating a cell from the sample, and subcloning the cell, wherein the cell is capable of replicating ASF virus; thereby isolating the cell.

55. The method of clause 47, further comprising culturing the cell in a growth medium comprising a growth factor composition.

56. The method of clause 55, wherein the growth factor composition comprises macrophage colony stimulating factor (MCSF) or granulocyte-macrophage colony stimulating factor (GMCSF).

57. The method of clause 55, wherein the growth factor composition comprises MCSF at a concentration of 5 to 10 ng/mL.

58. The method of clause 48, wherein the cell is a macrophage.

59. The method of clause 48, further comprising the step of culturing the cell for at least 5 passages.

60. The method of clause 48, wherein the porcine fetal subject is from about 30 to about 90 days of gestational age.

61. The method of clause 48, further comprising culturing the cell in a growth medium comprising a growth factor composition of MCSF or GMCSF.

62. The method of clause 54, wherein the cell is a macrophage.

63. The method of clause 54, further comprising the step of culturing the cell for at least 5 passages.

64. The method of clause 54, wherein the porcine fetal subject is from about 30 to about 90 days of gestational age.

65. The method of clause 54, further comprising culturing the cell in a growth medium comprising a growth factor composition of MCSF or GMCSF.

66. The method of clause 50, wherein the macrophage is an alveolar macrophage.

67. The method of clause 58, wherein the macrophage is an alveolar macrophage.

68. The method of clause 62, wherein the macrophage is an alveolar macrophage.

69. An isolated non-simian cell capable of reproducing the ASF virus, wherein the non-simian cell is obtained from an individual animal and cultured for at least 5 passages.

70. An isolated porcine fetal lung cell capable of infection by and/or reproducing the ASF virus.

71. The cell of clause 70, wherein the cell is an alveolar macrophage cell.

72. The cell of clause 70, wherein the cell is propagated in culture for at least 5 passages.

73. The cell of clause 70, wherein the cell is propagated in culture for at least 10, 20, and/or 50 passages.

74. An isolated primary cell or cell population obtained from a lung of a porcine fetus.

75. The cell or cell population of clause 74, wherein the fetus is from about 30 to about 90 days of gestational age.

76. The cell or cell population of clause 74, wherein the cell is an alveolar macrophage or the cell population comprises at least one alveolar macrophage cell.

77. An immortalized cell variant or derivative of the cell of any of clauses 69-71 and 74-76.

78. A cell or cell line designated as ZMAC.

79. A vaccine comprising the progeny of the ASF virus of clause 1 in a carrier.

80. The vaccine of clause 79, further comprising an adjuvant.

81. A method of eliciting an immune response against ASFV in a pig comprising administering to the pig the vaccine of clause 79.

82. The method of clause 81, wherein the vaccine is administered parenterally.

83. The method of clause 81, wherein the vaccine is administered orally.

84. The method of clause 81, wherein the vaccine is administered intranasally.

85. The method of clause 81, wherein the vaccine is administered mucosally.

EXAMPLES

Examples related to the present disclosure are described below. In some embodiments, alternative techniques can be used. The examples are intended to be illustrative and are not limiting or restrictive of the scope of the invention as set forth in the claims.

Example 1: Cell Materials and Growth of Cells

Cell materials. Cells from a porcine alveolar macrophage cell line designated as ZMAC-1 were prepared and deposited with a recognized International Depositary Authority, the American Type Culture Collection (ATCC; 10801 University Boulevard, Manassas, Virginia, United States of America) under the Budapest Treaty. The accession number is ATCC Patent Deposit No. PTA-8764 for cells characterized as being of *Sus scrofa* (pig/swine) lung tissue origin. According to the ATCC Certificate of Deposit document dated Dec. 7, 2007 (Budapest Treaty On The International Recognition Of The Deposit Of Microorganisms For The Purposes Of Patent Procedure; International Form; Receipt In The Case Of An Original Deposit Issued Pursuant To Rule 7.3 And Viability Statement Issued Pursuant To Rule 10.2), the Date of Receipt of Culture is Nov. 14, 2007 for ATCC® Patent Deposit Designation PTA-8764.

Growth of cells. In some embodiments, cells such as ZMAC-1 cells are cultivated in vitro. In general, principles of mammalian cell culture are applied. For example, cells can be cultured in the presence of antibiotics; gentamicin is used but not necessarily required.

Cells are prepared as follows. The culture medium is RPMI-1640 supplemented with 10% fetal bovine serum, sodium pyruvate (1 mM; Mediatech Cellgro, Cat. No. 25000-C1), non-essential amino acids (1×; Mediatech Cellgro Cat. No. 25-025-C1), and Gentamicin (50 mcg/ml; Gibco, Cat. No. 15750-060). The cells are maintained at cell concentrations of about 1 to 5×10e5 per ml. These cells generally grow in suspension. Discrete colonies of loosely adherent cells can develop but most of the cells will be growing in suspension. Normal cultures will produce floating cell clumps. To reduce adherence, the preferred type of culture flask is Sarstedt Tissue Culture Flask for suspension cell with PE vented cap (Cat. No. 83.1813.502). Established flasks can be harvested every 4-5 days with removal of ⅔ of the fluid and addition of fresh culture medium. New flasks are established by adding at least 3-6 million cells in a 20 ml volume in a T25 flask (minimum of 1.5×10e5 cells/ml). Growth can be enhanced by adding 2-10 ng/ml of macrophage colony-stimulating factor (mouse; Sigma-Aldrich Product No. M9170). Cell freezing can be accomplished by mixing equal volumes of ice-cold suspensions of cells at 4-8 million cells per ml and ice-cold freezing medium (90% serum, 10% DMSO). Chilled cryovials are filled with the cells suspended in freezing medium and maintained at ice-cold temperature during the process.

Figure 1:
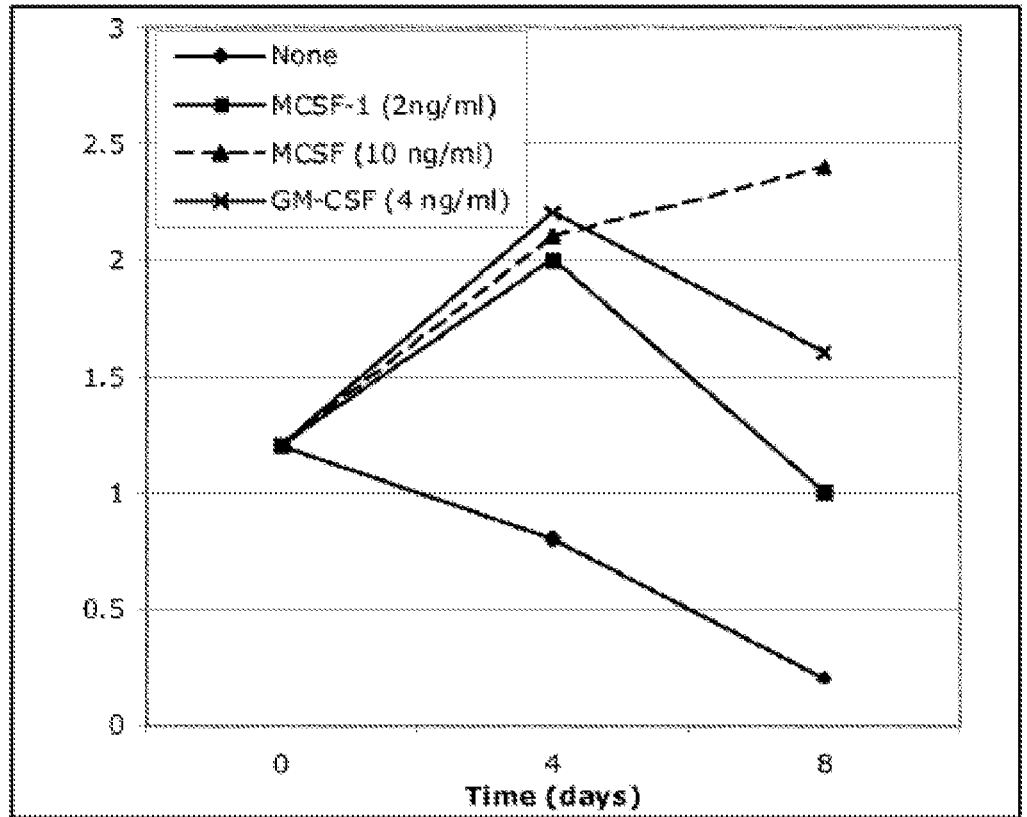
FIG. 1 shows growth of ZMAC-1 cells in the presence of growth factors according to an embodiment.

Referring now to FIG. 1, growth of ZMAC-1 cells in the presence of growth factors is shown. ZMAC-1 cells at $1.2\times10^5$ cell per ml were cultured for 8 days without exogenous growth factor or in the presence of the indicated concentration of either macrophage colony stimulating factor (MCSF) or granulocyte-macrophage colony stimulating factor (GMCSF). The cell concentration was determined with the aid of a hemocytometer at the fourth and eighth day of culture. The y-axis indicates cells/ml ($\times10^5$).

Example 2: Generation of Cell Materials and Methods of Isolation from Fetal Porcine Samples Further compositions and methods were developed. In an independent attempt, materials were derived from a sow at 60 days of gestation from the swine herd at the University of Illinois Veterinary Medicine Research Farm (identified as Sow number 5850). Following euthanasia, the uterus was aseptically removed from the abdominal cavity and transported to the cell culture laboratory. Manipulations were generally performed using a bio-safety cabinet under sterile conditions. Six fetuses were aseptically harvested from the uterus and placed in plastic Petri dishes. Lung organs, with the trachea intact and attached to the lung, were dissected away from the heart, esophagus and other membranes. The outside of the lung was thoroughly rinsed with sterile Hank's balanced salt solution (HBSS) to remove any visible blood and other contaminating remaining tissue. Cells in the airways of the lungs from each of the 6 fetuses were isolated separately by bronchoalveolar lavage by placing the lung in a clean and sterile Petri dish and filling the airways with 10 ml of sterile HBSS. The 10 ml of HBSS was propelled into the lung with the aid of a 10 cc syringe and a 1 inch 18 g needle, which was inserted through the lumen of the trachea. The fluid was gently propelled through the trachea while constraining it via compression with forceps to prevent backflow of the HBSS, resulting in the lungs becoming visibly inflated with the fluid. Afterwards the fluid containing the lung lavage cells was self-expelled from the lung by simply releasing the tracheal compression. The cell suspension collected in the Petri dish was transferred to a sterile 15 ml conical plastic tube and was underlaid with 3-4 ml of warm Ficoll-Hypaque 1077. Immediately afterwards cell suspension was purified via isopycnic centrifugation (400 g for 30 minutes at room temperature).

In an embodiment, cells can be purified by isopycnic centrifugation using Ficoll-Hypaque 1077 either the day of isolation or at a later time, e.g., 1, 2, or 3 weeks later. It is recognized that this purification procedure can facilitate removal of certain components such as red cells, and potentially other material, present in an original preparation. The band of cells obtained after centrifugation at the interface between the Ficoll-Hypaque 1077 and medium was harvested and washed with HBSS twice and the cells were recovered each time by centrifugation. After the second centrifugation, the recovered cell pellet from each fetal lung lavage was suspended in culture medium: RPMI-1640 supplemented with 10% fetal bovine serum, sodium pyruvate (1 mM; Mediatech Cellgro, Cat. No. 25-000-C1), non-essential amino acids (1×; Mediatech Cellgro Cat. No. 25-025-C1), and placed independently in one well of 6-well plate (Sarstedt) for suspension culture. Each well was labeled from 1-6 to identify the cells purified independently from each of the six fetuses. Although in this attempt very few and very small cells (<100) were recovered after the isopycnic centrifugation procedure, within 14 days after establishment of the initial cultures, significant growth was observed in every well. Since the macrophage progenitors harvested from the fetal lung were apparently very small and could have a density greater than 1.077 (thus going through the density medium to the bottom of the tube during the isopycnic centrifugation), in the case of fetus #1, the red cell pellet obtained after the isopycnic centrifugation was also harvested and placed in culture and labeled P1. In this case, although the predominant cell type at the initiation of the culture consisted of red blood cells, a small number of very small mononuclear cells was observed. At 16 and 24 days after the initiation of the culture the growth in cells derived from the lung lavage of fetus #4 exhibited sufficient growth to merit splitting into new wells of a 6 well plate. Cells derived from this culture were named ZMAC1107-4. Similarly, growth in the well labeled as P1, which was derived from the red blood cell pellet was clearly evident at 36 days after the initiation of the culture and was also split into 2 wells. Cells derived from this culture were named ZMAC1107-P1. The growth of cells was evident by the presence of cell clusters comprised of 2, 4, 8, 16 or more cells per cluster.

At 37 days after the initiation of the culture of the ZMAC1107-4, the culture medium for this cell line was supplemented in one of duplicate wells with 10 ng/ml of macrophage colony stimulating factor (mouse; Sigma-Aldrich Product No. M9170). Seven days later it was clear that the growth of the ZMAC1107-4 cells had been significantly aided at this early stage of culture by the exogenous supplementation with the growth factor, and thereafter the medium of all cultures was supplemented with MCSF at 5-10 ng/ml. Cultures are fed every 4-6 days by removing by aspiration half the volume of the cell culture and replacing it with fresh medium supplemented with the growth factor. The robust growth of both the ZMAC 1107-4 and ZMAC 1107-P1 lines was evident by the formation of cell colonies growing in suspension and loosely attached to the culture surface.

In another independent attempt, further compositions and methods were developed. A sow identified as number 9093, at 54 days of gestation was obtained from the swine herd at the University of Illinois Veterinary Medicine Research Farm. Following euthanasia, the uterus was aseptically removed from the abdominal cavity and transported to the cell culture laboratory. All manipulations from this point forward were done inside of a bio-safety cabinet under sterile conditions. Eight fetuses were aseptically harvested from the uterus and placed in plastic Petri dishes and their lungs, with the trachea intact and attached to the lung, dissected away from the heart, esophagus and other membranes. The outside of the lung was thoroughly rinsed with HBSS to remove any visible blood and other contaminating remaining tissue. Cells in the airways of the lungs from each of the eight fetuses were isolated separately by bronchoalveolar lavage by placing the lung in a clean and sterile Petri dish and filling the airways with 10 ml of sterile Hank's balanced salt solution (HBSS). The 10 ml of HBSS was propelled into the lung with the aid of a 10 cc syringe and a 1 inch 18 g needle, which was inserted through the lumen of the trachea. The fluid was gently propelled through the trachea while compressing it with forceps to prevent backflow of the HBSS, resulting in the lungs becoming visibly inflated with the fluid. Afterwards the fluid containing the lung lavage cells was self-expelled from the lung by simply reducing compression of the trachea. In some cases the lung was gently pressed down with the blunt end of scissors to help expel the remaining lavage fluid. The cell suspension collected in the Petri dish was transferred to a sterile 15 ml conical plastic tube, and centrifuged for 10 minutes at 1,500 RPM in a table top clinical centrifuge. The recovered cell pellet from each fetal lung lavage was suspended in culture medium: RPMI-1640 supplemented with 10% fetal bovine serum, sodium pyruvate (1 mM; Mediatech Cellgro, Cat. No. 25-000-C1), non-essential amino acids (1×; Mediatech Cellgro Cat. No. 25-025-C1) and placed independently in one well of 6-well plate (Sarstedt) for suspension culture. Each well was labeled from 1-8 to identify the cells purified independently from each of the eight fetuses. Approximately 10,000 cells were initially placed in culture from each fetal lung lavage. Growth in these cultures was evident by 5 days. Large clumps of cells were evident in cultures derived from fetuses #1, 3, 6, 7 and 8.

At 12 days after the initiation of the culture, the non-adherent and loosely adherent cells from all 8 fetal lung lavage cell cultures were harvested by gently pipetting and purified by isopycnic centrifugation using Ficoll-Hypaque 1077. This was accomplished by transferring the cell suspension to a sterile 15 ml conical plastic tube, which was underlay with 3-4 ml of warm Ficoll-Hypaque 1077 and then centrifuged at 400 g for 30 minutes at room temperature. A clearly visible band of cells was obtained after centrifugation at the interface between the Ficoll-Hypaque 1077. Medium was harvested and washed with HBSS twice, and the cells were recovered each time by centrifugation. After the second centrifugation, the recovered cell pellet from each individual fetal lung lavage culture was suspended in 3 ml of culture medium: RPMI-1640 supplemented with 10% fetal bovine serum, sodium pyruvate (1 mM; Mediatech Cellgro, Cat. No. 25-000-C1), non-essential amino acids (1×; Mediatech Cellgro Cat. No. 25-025-C1), and placed independently in one well of 6-well plates (Sarstedt) for suspension culture and labeled 1-8, which corresponded directly to the original labeling of the cultures. Five days later all cell cultures were fed 2 cc of fresh culture medium. Nine days later significant growth of cells in suspension as well as adherent cells was evident in cultures derived from fetal lung lavage cell cultures labeled 3 and 6, which exhibited a significant number of macrophage colonies growing in suspension as well as loosely adherent round macrophages. A number of large spherical syncytial cells, surrounded by small macrophages forming a structure appearing as a cellular crown, were observed. At 26 days after the beginning of the culture, the cell cultures were fed fresh medium supplemented with 5 ng/ml of MCSF (mouse; Sigma-Aldrich Product No. M9170). Five days later vigorous growth of cell macrophage colonies growing in suspension as well as loosely adherent on the surface of the culture plate was observed in cultures derived from fetuses #3, #6 and #8. These lines were named ZMAC1207-3, ZMAC1207-6, and ZMAC1207-8 respectively and were expanded a few days later by transferring to T75 flasks in culture medium supplemented with 5-10 ng/ml of MCSF.

Example 3: Establishing ZMAC Cell Cultures at The Pirbright Institute and Testing for ASFV Susceptibility A vial of ZMAC cells provided by Aptimmune Biologics, Inc. (1005 N. Warson Road, Suite 305, St. Louis, MO 63132) was revived from liquid nitrogen storage. Briefly, the cells were thawed quickly at 37° C. (i.e., degrees Celsius), added to 10 ml warm culture medium, centrifuged 7 minutes at 330×g and 4° C. to remove freezing medium and then cultivated in a total of 50 ml medium and 5 ng/ml MCSF in T75 ultra low adherence (ULA) flasks. After 3 days, the culture was re-fed with new medium for a 1:2 dilution, with M-CSF supplementation for a final concentration of 5 ng/ml in the total volume (100 ml). Additional re-feedings were made with fresh medium (prepared less than seven days before) for 1:2 dilution of the culture volumes with M-CSF supplementation for a final 5 ng/ml, at every three to four days. When the cultures reached approximately 150 ml in the T75 ULA flasks, the culture was divided into a new flask, and re-fed as before every three to four days. Following this procedure, in one month three T75 ULA flasks with growing ZMAC cultures were established. Cell count in the three flasks revealed approximately $3\times10^6$ cells per flask. From this point on, part of the cells were kept on the same T75 ULA flasks or expanded to a few new T75 ULA, and re-fed following the same scheme. When reaching approximately 150 ml culture volume in the flasks, the cells were collected by centrifugation, counted and part re-seeded in the same flasks (approximately $4\times10^4$ cells/ml seeded, 1.2 to $2\times10^6$ cells per flask). Part of the cells were used for preparing new frozen stocks of cells (with $3.5$-$5\times10^6$ cells/ml in 90% fetal calf serum and 10% DMSO) or for testing alternative culture vessels. In the span of two months since the beginning of the ZMAC culture, it was possible to obtain eight cryovials of frozen cells. Two of these were successfully revived and the cells expanded into new flasks, showing that the conditions used for freezing the cells were adequate.

Cultivation in 250 ml polycarbonate Erlenmeyers (Corning ref. 43114) beginning with approximately $1.2\times10^6$ cells in 50 ml medium and 5 ng/ml MCSF ($2.4\times10^4$ cells/ml) revealed that this is also a good vessel for the ZMAC cultures using a similar feeding scheme as with the T75 ULA, with the cell number increasing four times in thirteen days with 125 ml culture volume at the end.

Following cultivation of ZMAC cells and up-scaling of the cultures to larger vessels, the ZMAC cultures were fed from this point on at a minimum interval of three days and the M-CSF concentration increased to 10 ng/ml. Additionally, the initial seeding cell concentration in the T75 ULA recommended is $6\times10^4$/ml. Following these new instructions, cells in T75 ULA cultures and 250 ml Erlenmeyers were usually observed to triplicate or quadruplicate in 7-9 days. In another 2 months approximately, using these growth conditions the inventors could obtain an extra eight cryovials of cells and other two vials used for re-initiating new cultures following growth difficulties. The inventors have available a total of 12 cyrovials with ZMAC cells that the inventors have propagated. The inventors also observed that inactivation of the fetal calf serum (component of the complete culture medium) for longer than 30 minutes at 56 degrees is detrimental for the ZMAC culture, leading to poor cell growth. Therefore, the inventors are now using the recommended serum without heat inactivation.

ZMAC cells were used in preliminary assays to test their susceptibility to ASFV and supported viral growth. Titrations of different ASFV isolates were performed in parallel in 96-well format, either using normal adherent tissue culture plates or ULA plates (Corning 4515-96 well Spheroid Microplate) with $2.2 \times 10^6$ ZMAC cells per plate ($2.3 \times 10^4$ cells per well) and the complete medium supplemented with M-CSF. The same titrations were made with porcine bone marrow (PBM) cells on 96-well tissue culture plates, the classical titration method for ASFV, for comparison. As shown in TABLE 1, there was a significant increase of at least one log in titers from the ZMAC cells in ULA plates in comparison to the ZMAC cells in normal adherent tissue culture plates, suggesting that adherent ZMAC cells lose some susceptibility to ASFV. The titers in the ULA vessel were also more approximated to the ones obtained in PBMs, except for the NHV isolate, which presented a 2 log higher titer in the ZMAC cells.

TABLE 1

Comparison of Titrations Performed on ZMAC Cells and Porcine Bone Marrow Cells of Different ASFV Isolates ($TCID_{50}/ml$)

| | ZMAC adherent | ZMAC ULA plate | PBM |
|---|---|---|---|
| OURT 88/3 | $3.16 \times 10^6$ | $6.81 \times 10^7$ | $3.16 \times 10^7$ |
| NHV | $6.81 \times 10^2$ | $3.16 \times 10^5$ | $3.16 \times 10^3$ |
| Georgia 2007/1 | $3.16 \times 10^5$ | $3.16 \times 10^6$ | $1.47 \times 10^7$ |

Example 4: Optimization of Cell Culture Conditions for Scale Up of ZMAC Cell Culture Several types of culture medium as well as modifications in the concentration of components of these media were examined in order to identify the optimal culture conditions for the ZMAC cell line. Modifications to RPMI-1640 consisting of the increase of glucose and glutamine concentration were found to optimize the rate of growth of ZMAC cells. Splitting the cell culture every four to five days by the addition of murine recombinant macrophage colony stimulating factor (MCSF) at a final concentration in a range of 5-20 ng/mL and sufficient volume of fresh medium to achieve a dilution of culture medium volume of 1:3 was found to be optimal. Under these conditions a cell concentration of $0.5$-$0.8 \times 10^5$/ml after dilution was maintained at the time of splitting and reaching a cell concentration of $1.4$-$1.6 \times 10^5$/ml four to five days later. A single addition of 1 ng/ml of porcine recombinant granulocyte macrophage colony stimulating factor (GMCSF) after 10 passages was found to help maintain the vigorous growth of the cells after 10 passages, which then maintained their growth vigor for at least 10 more cell passages.

The ZMAC cells are adherent, and if cultured on a tissue culture-treated surface, the cells will become firmly attached. However, for some undetermined reason, firm attachment of the ZMAC cells to a culture surface significantly slows down the rate of cell growth. In contrast, if the cells are cultured on a culture vessel that does promote their adherence, the ZMAC cells grow efficiently as loosely adherent colonies. This feat can be accomplished by simply using a non-tissue cultured treated vessel or a vessel with a hydrophobic surface designed for suspension culture (Sarstedt flasks for suspension culture, cat no. 83.1810.502). The inventors have found that the type of tissue culture vessels that optimally promotes ZMAC cell growth are the Corning® Ultra-Low attachment (ULA) cell culture flasks. Unfortunately, this vessel is expensive and is not appropriate for economical and practical scale up since the largest size of flask manufactured has a 75 cm² growth area. Regardless, the inventors have developed a standard protocol to initiate ZMAC cell culture starting from a frozen aliquot of ZMAC cells. In this case it is optimal to use Corning's ULA flasks for initial expansion and production of several of these flasks. Then, medium scale up can be achieved by transitioning to a larger vessel such as a Sarstedt's suspension culture flasks with a 175 cm² growth area.

Figure 2:
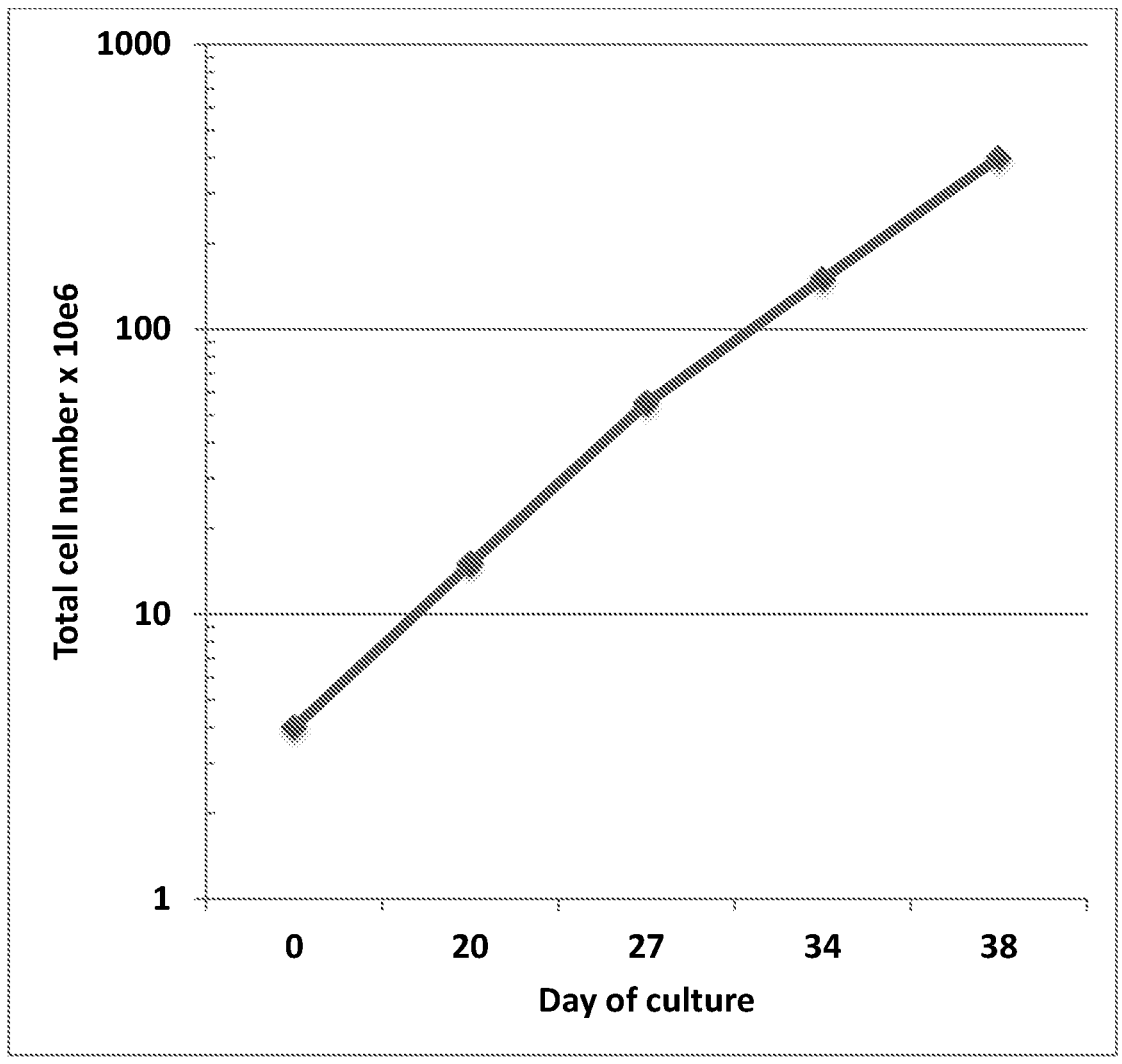
FIG. 2 shows ZMAC cell yield according to an embodiment.

A typical production run starting with a frozen aliquot of ZMAC cells containing $4 \times 10^6$, consisted of initially establishing a 75 cm² ULA tissue culture flask (Corning) with the thawed cell from such vial put into culture in a 35 ml volume of modified RPMI-1640 culture medium supplemented with 10% fetal bovine serum and 5 ng/ml of murine MCSF. After expansion of the cells to establish two ULA 75 cm² flask within 16-20 days containing a total volume of 150 ml of cell suspension per flask. Further expansion of the volume of cell culture was accomplished by using regular 300 cm² tissue culture flasks, which allowed a >300 ml volume of culture per flask. However, in this case in order to minimize the cell adherence, the flask was positioned in the incubator so that the non-tissue culture treated side of the flask was facing down so that the cells settled by gravity on the non-tissue culture treated internal surface of the flask. Referring now to FIG. 2, under these conditions and after 7 cell passages, a 100-fold expansion of cell number was achieved within 38 days. The y-axis shows total cell number×10e6, and the x-axis shows day of culture. Subsequent expansion by passage of the cells at a 1:3 dilution every 4-5 days should result on a 2-3-fold expansion in cell number. Thus, improvement in the method of culture has been made which allows >20 sequential passages of the cell line starting from a worker cell seed stock of the cell line. More recently, further refinements on the formulation of the culture medium have resulted on a two-fold increase in cell yield per volume of culture, which is accompanied by a corresponding increase in the rate of cell growth. This most recent improvement will not only reduce the cost of production but also provides an indication that further optimization of the culture process will be realized during the development of the method of cell culture for the process of industrial scale up.

In this regard, several types of cell culture vessels were tested for their suitability to enable efficient ZMAC cell growth. These included the use of disposable bioreactors, cell culture bags such as the JRH polyethylene bags, as well as larger culture vessels with volume capacities ranging from 0.5-10 L. The need for a stirred versus static culture was also explored. These studies revealed that the cells do not require stirring. Rather, it is apparent that the cells grow best when they are allowed to settle and be in close contact with each other. These tests revealed that several inexpensive types of vessels are suitable for efficient medium scale culture of the ZMAC cells that should allow at least initial medium scale commercial production of vaccine. The inventors have a prototype culture system that enables a continuous method of ZMAC cell culture in which cells can be harvested from these established culture vessels and then transferred to other vessels more suitable for virus production and compatible with vaccine production. Re-feeding of the established culture vessels allows for rapid expansion of the ZMAC cell population within 3-4 days for another round of cell harvest. Currently, it appears that this process can be repeated indefinitely provided that the cells are maintained under optimal conditions of culture.

Example 5: A Porcine Macrophage Cell Line that Supports High Levels of African Swine Fever Virus Replication The main target cells for ASFV replication in pigs are of monocyte macrophage lineage and express markers typical of the intermediate to late stages of differentiation. The lack of a porcine cell line, which accurately represents these target cells, limits research on virus host interactions and the development of live-attenuated vaccine strains. The inventors show here that the continuously growing, growth factor dependent ZMAC-4 porcine macrophage cell line is susceptible to infection with eight different field isolates of ASFV. Replication in ZMAC-4 cells occurred with similar kinetics and to similar high titers as in primary porcine bone marrow cells. In addition, the inventors showed that twelve passages of an attenuated strain of ASFV, OURT88/3, in ZMAC-4 cells did not reduce the ability of this virus to induce protection against challenge with virulent virus. Thus, the ZMAC-4 cells provide an alternative to primary cells for ASFV replication.

Introduction

ASFV causes a hemorrhagic fever in domestic pigs and wild boar that can result in death of almost all infected animals. The disease is caused by a large DNA virus that is the only member of the Asfarviridae family and has a genome length of 170 to 193 kbp varying between isolates. ASFV is present in a wildlife cycle in E. Africa involving warthogs and soft tick vectors of *Ornithodoros* spp, which are persistently infected with few if any clinical signs. Following the introduction of ASFV in 2007 to Georgia in the Trans Caucasus region, the disease has spread to Russia and further west in Europe infecting a further 11 countries (OIE WAHIS https://www.oie.int/wahis_2/public/wahid.php/Diseaseinformation/diseasehome). In 2018, the first ASFV outbreak was detected in China and rapidly spread over large distances reaching all provinces by the first part of 2019. Further spread to 8 additional countries in Asia has resulted in increased global risk and extended the economic impact of the outbreaks. The absence of a vaccine limits options for control of ASFV. Although efforts to develop a vaccine are increasing, a lack of knowledge about the virus and its interaction with the host hinders this process.

ASFV replicates primarily in cells of the monocyte macrophage lineage which express markers typical of the intermediate to late stages of differentiation. By manipulation of the function of these cells the virus can interfere with and modulate the host's response to infection. Better understanding of this interaction will provide information on mechanisms of virus immune evasion and pathogenesis, thus, underpinning vaccine development. The availability of a biologically relevant cell line to pursue these studies would boost research by providing a genetically homogenous cell line. In addition, this cell line would provide an option for production of live attenuated vaccines for ASFV and alternatives to primary macrophage cultures for diagnosis and virus isolation. Previously established cells lines including Vero, Cos, and WSL have been used to propagate ASFV but an adaptation of the virus to replicate in these cells is required. This can result in modification of the genome which may reduce replication in porcine macrophages or pigs. Additionally, these established cells differ in many important ways from macrophages in how they respond to infection.

The ZMAC-4 pig macrophage cell line was derived from fetal pig lung macrophages. The inventors here describe experiments which demonstrate that ASFV isolates replicate in the ZMAC-4 cell line to levels similar to primary porcine macrophages without any adaptation step to the cell line. In addition, the inventors show that passage of the live attenuated ASFV strain OURT88/3 in ZMAC-4 cells did not reduce the efficacy of this virus in inducing 100% protection in pigs against challenge with a virulent virus OURT88/1. These findings indicate the ZMAC-4 cell line provides a suitable cell line for research, diagnosis, and production of live attenuated ASFV vaccines.

Materials and Methods

Viruses and Cells

The OURT88/3 and NH/P68 genotype I non-hemadsorbing attenuated ASFV strains, virulent strains genotype I OURT88/1, Benin97/1, Georgia genotype II, Malawi LIL 20/1 genotype VIII, and moderately virulent strain Dominican Republic strains have been described previously. Other ASFV isolates used were available in the reference collection at The Pirbright Institute. These viruses were obtained from outbreaks in domestic pigs or isolated from ticks in the field and grown in primary porcine bone marrow cell cultures for a maximum of 3 passages.

The cell line ZMAC-4 was derived from the lungs of a porcine fetus, and consists of non-transformed phagocytic cells that require the presence of MCSF to grow. The cell is oligoclonal and stable, as demonstrated by its ability to be successfully passaged for more than 75 times over a period of 8 months without exhibiting a decrease in proliferation capacity. ZMAC-4 cells were obtained from Aptimmune Biologics, Inc. or the University of Illinois.

Flow Cytometry

Staining of suspensions of ZMAC-4 cells for flow cytometry consisted of incubations in Flow PBS (PBS, 1.0% BSA, 0.01% sodium azide) containing the indicated mAbs for 30 min at ice-cold temperature with each step being terminated by one wash with Flow PBS. Initially, ZMAC-4 cells were left untreated or were separately exposed to one of the following monoclonal antibodies that recognize the indicated porcine molecule: CD14 (biG 10/14), CD163 (2A10/11), CD172 (74-12-55), CD203a (PM18-7), PU.1 (E.388.3). Afterwards, the cells were sequentially incubated in Flow PBS containing goat anti-mouse Ig conjugated to PE (Southern Biotech), 2% normal mouse serum (Sigma) and 100 mg/ml mouse IgG (Zymed Laboratories, Invitrogen). To detect PU.1, cells were fixed with paraformaldehyde and permeabilized with detergent as previously described. To detect phagocytic activity, ZMAC-4 cells were incubated in the presence of Fluoresbrite YG microspheres 2.00 micrometer (Polysciences, Inc) for 30 minutes at 37° C. in culture medium. As a control, ZMAC-4 cells were incubated with the same particles at ice cold temperature in the presence of 1% Sodium Azide. Background fluorescence in this assay was detected using cells not exposed to the microspheres. Flow cytometric analysis was performed with an LSR II flow cytometer (BD Biosciences, San Jose, CA, USA). Data analyses and preparation of graphical representations were done with FlowJo software (Ashland, OR, USA).

Virus Infection and Titration

ASFV was titrated by limiting dilution in cultures of porcine bone marrow cells and infection detected by hemadsorption assay (HAD) or by immunofluorescence using a monoclonal antibody against the p30/pCP204L protein as described previously. Evaluation of ASFV growth in ZMAC-4 cells was carried out as described previously. Infections were made with a multiplicity of infection (MOI) 0.05 of Georgia 2007/1 and the cells were frozen at –80° C. after the different infection times. The cells were subjected to two freeze-thaw cycles before titration in parallel on porcine bone marrow cells from the same pig. Titers, as $TCID_{50}$/ml (tissue culture infectious dose 50% level), were obtained by immunofluorescence as stated herein and HAD titers were obtained by addition of erythrocytes, collected from heparinized pig blood, together with the inoculum. Titrations (in triplicate wells) were made in parallel using cells from the same culture passage.

Virus Genome Detection

DNA was extracted from whole blood collected in EDTA or tissues collected at post-mortem as described previously and detected by qPCR as described previously.

Animal Experiments

Experiments were carried out in SAPO4 high containment facilities at The Pirbright Institute and regulated by the Animal (Scientific Procedures) Act UK 1986. Large White and Landrace cross-bred pigs 8-9 weeks old (18 to 22 kg) from a high health status farm were used in the experiment.

Results

Features of ZMAC-4 Cells

Figure 3:
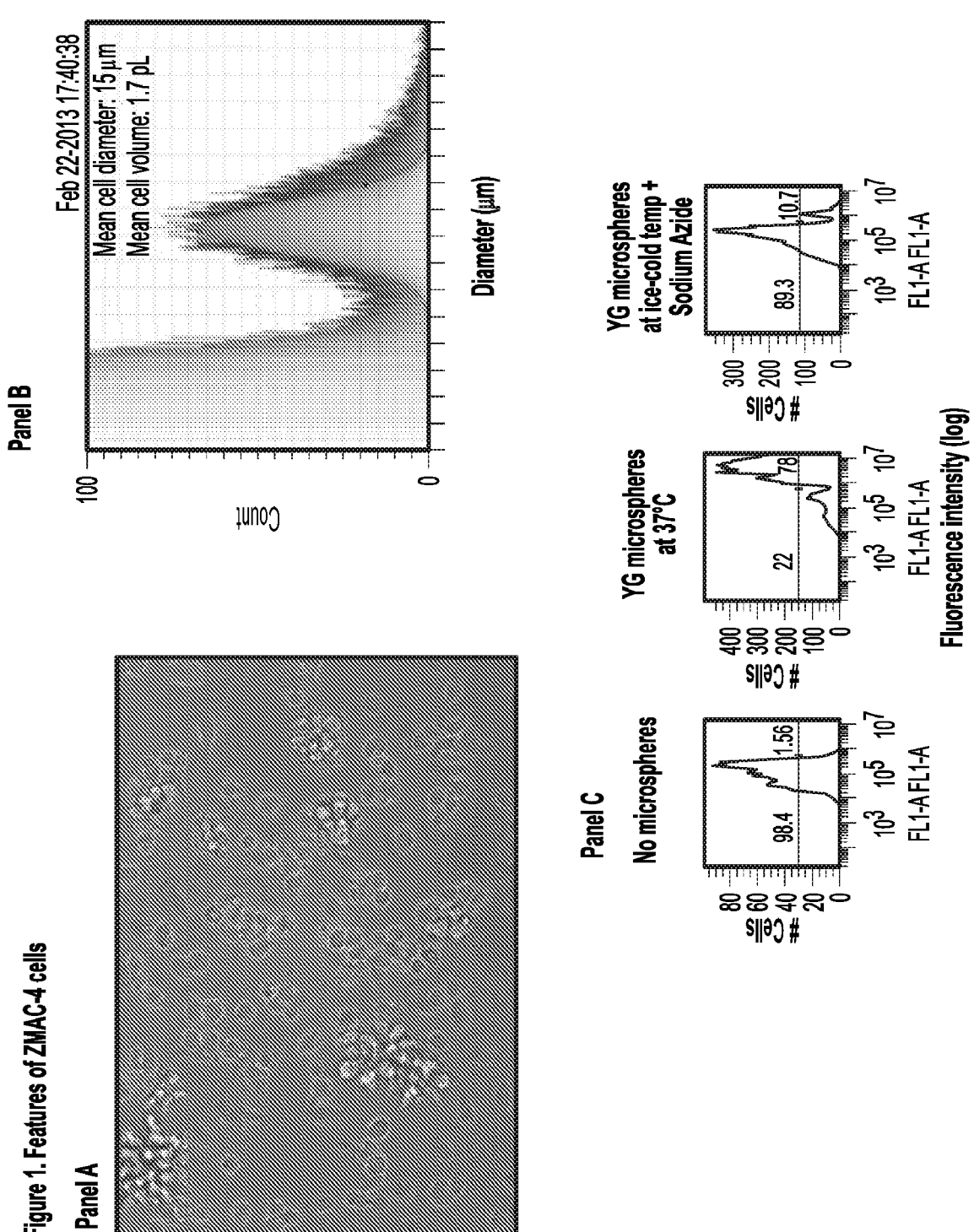
FIG. 3 shows various features of ZMAC-4 cells according to an embodiment.
Figure 3:
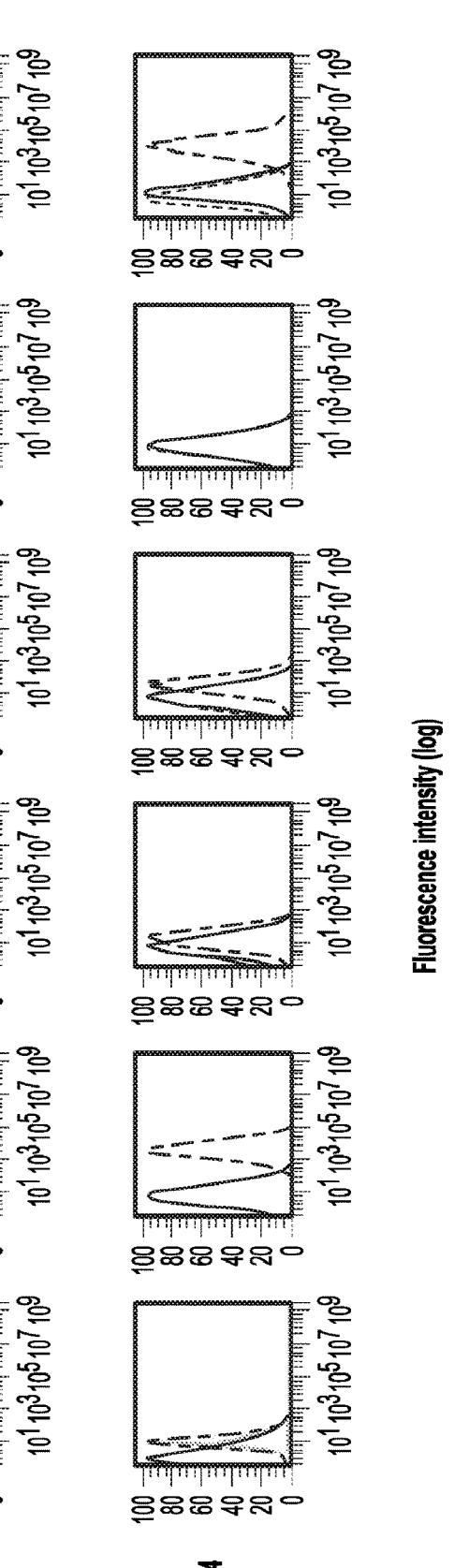

Referring now to Panel A in FIG. 3, morphology of ZMAC-4 cells was evaluated. Live cultures of ZMAC-4 cells were imaged with an inverted phase contrast microscope. Original magnification is 40×. Morphologically the ZMAC-4 cells exhibit the presence of *filipodia* and *lamellipodia*. Referring now to Panel B in FIG. 3, mean cell diameter and volume of ZMAC-4 cells was determined with a Moxi Z instrument using a type S cassette. The ZMAC-4 cells have a mean cell diameter of 15 µM and a mean cell volume of 1.7 µL. The graph represents the analysis of 75,000 cells. Referring now to Panel C in FIG. 3, phagocytic activity of ZMAC-4 cells was evaluated. Panel C shows results from flow cytometric analysis of cells that were left untreated (no beads), or exposed YG microspheres for 30 minutes at either 37° C. or at ice cold temperature in the presence of 1% Sodium Azide. The analysis of the ZMAC-4 cells demonstrates that such cells are phagocytic. Referring now to Panel D in FIG. 3, flow cytometric analysis of primary porcine alveolar macrophages (top row) or ZMAC-4 cells (bottom row) reacted with antibodies specific for the indicted molecule is shown. The ZMAC-4 cells uniformly express several surface markers characteristic of porcine alveolar macrophages (PAM) including CD14, CD163, and CD172, AsGM1, as well as E-twenty-six (E26)-family transcription factor PU.1 PU.1 is an E-twenty-six (E26) transformation-specific family transcription factor that plays a pivotal role in normal myeloid differentiation. It is most prominent in myeloid cells and involved in the development and maturation of B cells, macrophages, and neutrophils. Thus, the expression of PU.1 is a hallmark of macrophages. Notably the ZMAC-4 cells do not appear to express SWC9/CD203a. The lack of CD203a likely indicates that the ZMAC-4 cells are not as mature as primary alveolar macrophages. This is expected since the ZMAC-4 cells are able to proliferate, while primary alveolar macrophages do not. Previous results showed that the ZMAC-4 cells produce IFN-α in response to polyIC with similar kinetics as PAMs. Thus, the ZMAC-4 cells exhibit a number of characteristics typical of PAMs.

ASFV Replicates to Similar Titers in ZMAC-4 Cells as Primary Porcine Bone Marrow Cells.

In order to test the susceptibility of ZMAC-4 cells for infection by field strains of ASFV, infections in these cells were compared with primary macrophage cultures derived from pig bone marrow (PBM). To assess the infection susceptibility with field isolates of ASFV, the same virus stocks of 8 field isolates of ASFV (OURT88/3, NH/P68, Benin 1997/1, Georgia 2007/1, Malawi LIL20/1, Tengani, MOZ 94/1, ZOM 2/84, Dominican Republic) from genotypes I, II, VIII were titrated in triplicate in parallel in ZMAC-4 and PBM cells. The results in TABLE 2 showed that titrations in ZMAC-4 cells reached similar levels in comparison to those in PBM cells for all the isolates tested. These results indicated that the ZMAC-4 cells are similarly susceptible to infection as primary porcine macrophages.

TABLE 2

Titration of Different ASFV Isolates on Primary Porcine Bone Marrow Macrophages and ZMAC Cells

| | Genotype | PBM (TCID50/ml) | ZMAC (TCID50/ml) |
|---|---|---|---|
| OURT 88/3 | I | $3.16 \times 10^7$ | $6.81 \times 10^7$ |
| NH/P68 | I | $3.16 \times 10^3$ | $3.16 \times 10^5$ |
| Benin 1997/1 | I | $1.47 \times 10^7$ | $3.16 \times 10^7$ |
| Georgia 2007/1 | II | $3 \times 10^6$ | $3 \times 10^6$ |
| Malawi LIL 20/1 | VIII | $7 \times 10^6$ | $7 \times 10^6$ |
| Tengani | | $3 \times 10^6$ | $1 \times 10^7$ |
| MOZ 94/1 | II | $1 \times 10^7$ | $1 \times 10^7$ |
| ZOM 2/84 | VIII | $3 \times 10^5$ | $3 \times 10^4$ |
| Dominican Republic | I | $3 \times 10^5$ | $3 \times 10^4$ |

Figure 4:
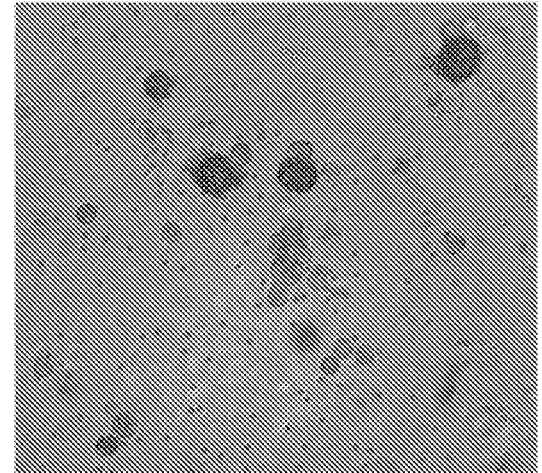
FIG. 4 shows infection of ZMAC-4 cells with ASFV according to an embodiment.
Figure 4:
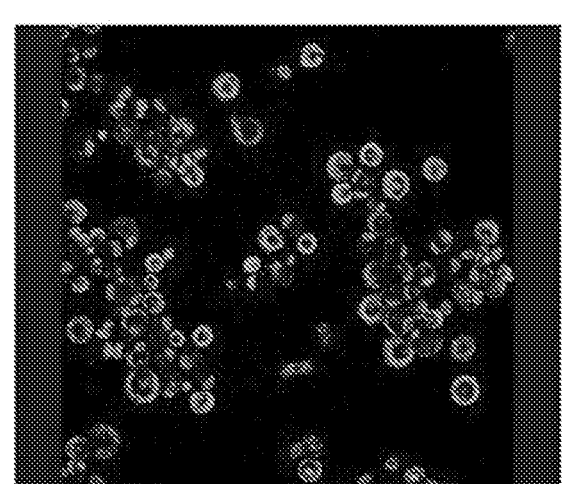

To determine the effectiveness of titration by hemadsorption (HAD/ml) in ZMAC-4 cells compared to indirect immunofluorescence (against viral early protein P30—TCID50/ml), different field isolates of ASFV NH/P68, Georgia 2007/1 and Benin 97/1 were titrated in parallel on ZMAC-4 cells with erythrocytes added to the culture medium. For $TCID_{50}$ titers, the cells were stained for immunofluorescence detection of P30 early viral protein and observed under the fluorescence microscope; for determining titers as HAD50 inoculum was added to the cells together with pig erythrocytes and screened under the optical microscope for the presence of hemadsorption rosettes at the different dilutions. The cells were observed under the microscope 3 days after inoculation similarly to previous titrations. Referring now to FIG. 4, the presence of hemadsorption rosettes at different inoculum dilutions was screened and the titers obtained, as shown in TABLE 3, demonstrated similar results using both titration techniques except for the non-hemadsorbent isolate NH/P68, which as expected didn't induce hemadsorption. This isolate has interruptions in the genes coding for the CD2v/EP402R and C-type lectin/EP153R genes explaining its non-hemadsorbing phenotype. Infection rates of up to 80% of the cells were achieved as estimated by immunofluorescence as shown in FIG. 4.

TABLE 3

Titration of ASFV Field Isolates on ZMAC Cells by Indirect
Immunofluorescence (TCID50) and Hemadsorption (HAD50)

|  | TCID50/ml | HAD/ml |
|---|---|---|
| NH/P68 | $3.16 \times 10^5$ | 0 |
| Georgia 2007/1 | $3.16 \times 10^6$ | $7.9 \times 10^6$ |
| Benin 1988/1 | $3.16 \times 10^7$ | $1.83 \times 10^7$ |

Dynamics of ASFV Replication in ZMAC-4 Cells Compared to PBM Cells.

Figure 5:
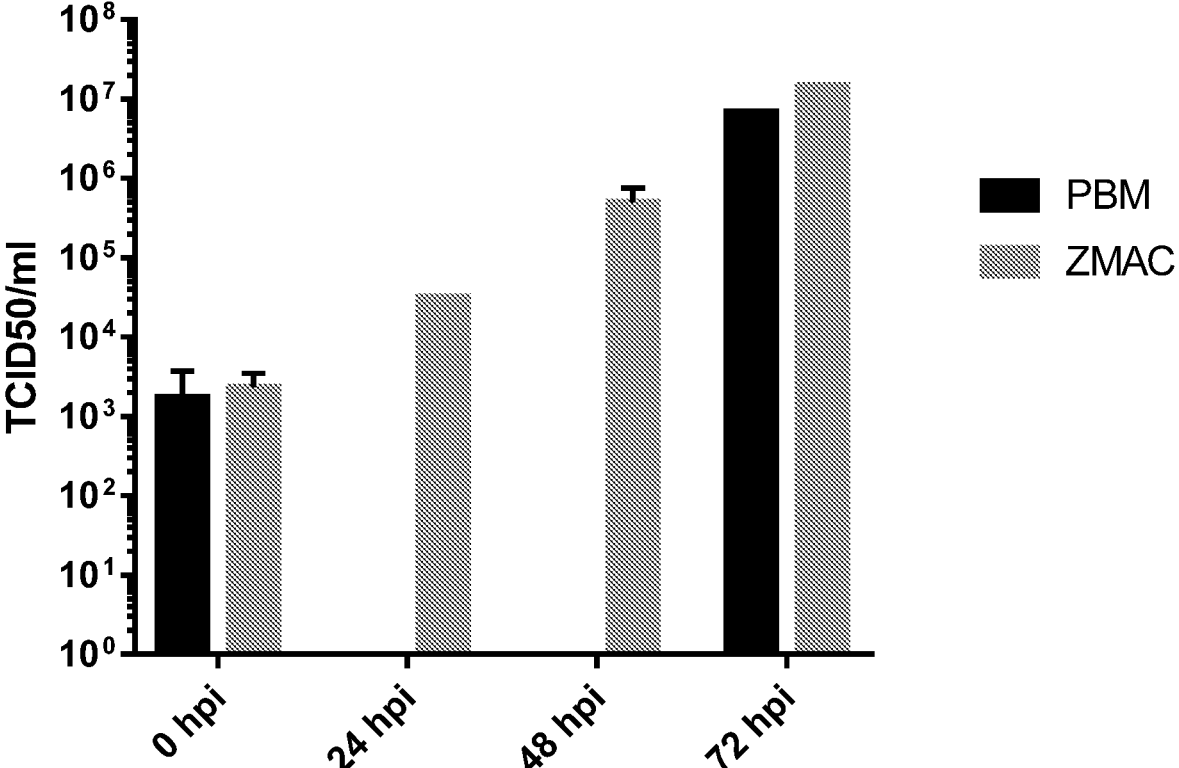
FIG. 5 shows ASFV-Georgia 2007/1 titers obtained in ZMAC and porcine bone marrow (PBM) cultures along a 72 h infection period according to an embodiment.

Referring now to FIG. 5, ASFV progeny production was compared after infections on PBM cultures and ZMAC-4 cultures. The y-axis in FIG. 5 shows titers, and the x-axis shows hours post infection. $2 \times 10^5$ ZMAC cells in 0.5 ml culture medium were transferred to 5 ml polypropylene tubes (Corning 352063) and inoculated with ASFV-Georgia at an MOI of 0.001. In parallel, PBM cultures in 24-well tissue culture plates with 0.5 ml medium per well were also inoculated at a similar MOI. Infections were made with the same virus stock of Georgia 2007/1 at low MOI (0.05) in both cell types and virus growth was monitored at 0, 24, 48, and 72 h in the ZMAC-4 cells and at 0 and 72 h in PBMs. Titers in ZMAC-4 cells increased progressively and reached approximated titers to the PBM cultures after 72 h ($1.47 \times 10^7$/ml in ZMAC-4 and $6.81 \times 10^6$/ml in PBM), proving the high susceptibility of the ZMAC-4 cells to ASFV infection and effective production of the virus.

Figure 6:
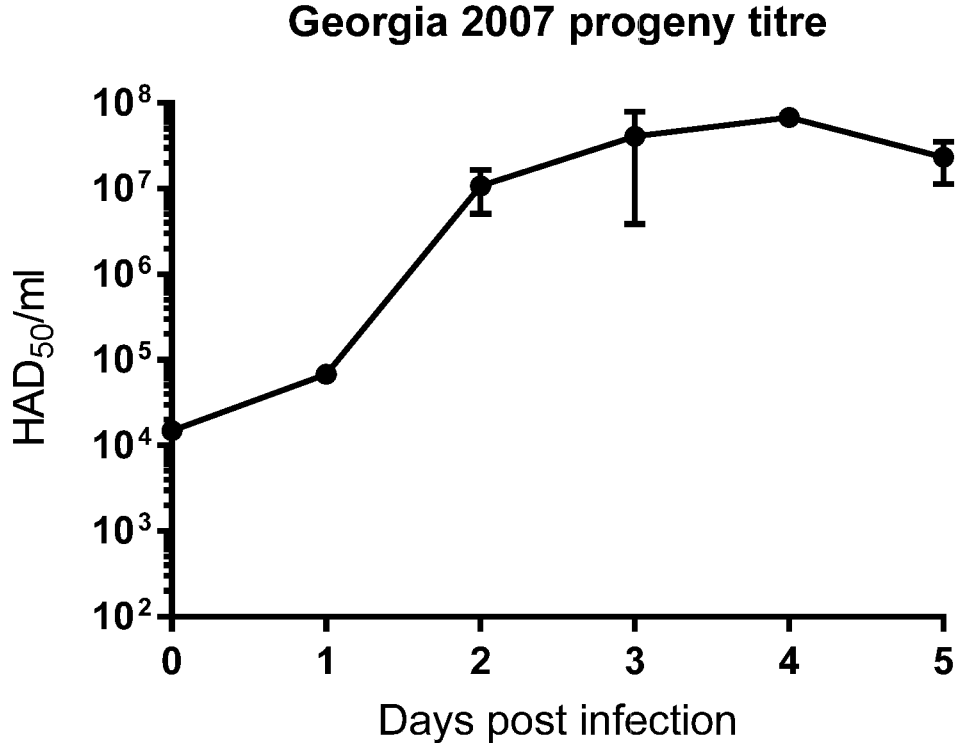
FIG. 6 shows progeny virus titers along five days of infection in ZMAC cells according to an embodiment.

Now referring to FIG. 6, the inventors also assessed how long the ZMAC-4 cultures could sustain ASFV growth. The y-axis in FIG. 6 shows titers, and the x-axis shows days post infection. Infections were made at a low MOI 0.05 and virus progeny production was titrated over a period of five days. FIG. 6 shows ASF growth in ZMAC-4 cells over 5 days. Progeny titers increased more than 3 Log units after inoculation until 4 days of culture (from $1.48 \times 10^4$ to $6.76 \times 10^7$ HAD50/ml) when such titers reached a maximum titer, decreasing slightly at day five ($2.32 \times 10^7$ HAD50/ml). Therefore, four days of infection seem to be optimal for obtaining a maximal viral yield with ZMAC-4 cells. Passage of ASFV Live Attenuated Strain OURT88/3 in ZMAC-4 Cells Does Not Reduce the Induction of a Protective Response Against Challenge with Virulent ASFV in Pigs.

To determine if passage of ASFV in ZMAC-4 cells altered immunogenicity of the virus in pigs, the inventors cultured the attenuated genotype I strain OURT88/3 for 12 passages in ZMAC-4 cells using a low multiplicity of infection (MOI of 0.1). Titers of virus recovered at each passage were similar. The virus harvested after the 12th passage was used to immunize pigs as described below.

Groups of 6 outbred pigs obtained from a high health status farm were inoculated intramuscularly (IM) with $10^4$ TCID$_{50}$ (tissue culture infectious dose 50% level) of the OURT88/3 strain at IAH-Pirbright in SAPO4 containment. One group (Group 1) was inoculated intra-muscularly with $10^4$ TCID$_{50}$ of the parental OURT88/3 isolate before passage. The other group (Group 2) was inoculated intra-muscularly with $10^4$ TCID$_{50}$ of the OURT88/3 isolate that had been passaged 12 times in ZMAC-4 cells at IAH-Pirbright in SAPO4 containment. Pigs were monitored daily for clinical signs and scored according to the standard the inventors have utilized (e.g., King K, Chapman D, Argilaguet J M, Fishbourne E, Hutet E, et al. 2011. Protection of European domestic pigs from virulent African isolates of African swine fever virus by experimental immunization. *Vaccine* 29: 4593-600). At 21 days post-inoculation the pigs in both Group 1 and Group 2 were challenged with virulent isolate OURT88/1 intramuscularly with $10^4$ TCID$_{50}$. Another group (Group 4) of three control pigs which had not been immunized with OURT88/3 (naïve non-immune pigs) were also challenged with virulent strain OURT88/1. Blood samples were collected weekly before challenge with OURT88/1 and at 3 day intervals post-challenge for measurement of viremia by qPCR. Post-mortems were conducted at termination and tissue samples were collected.

Figure 7:
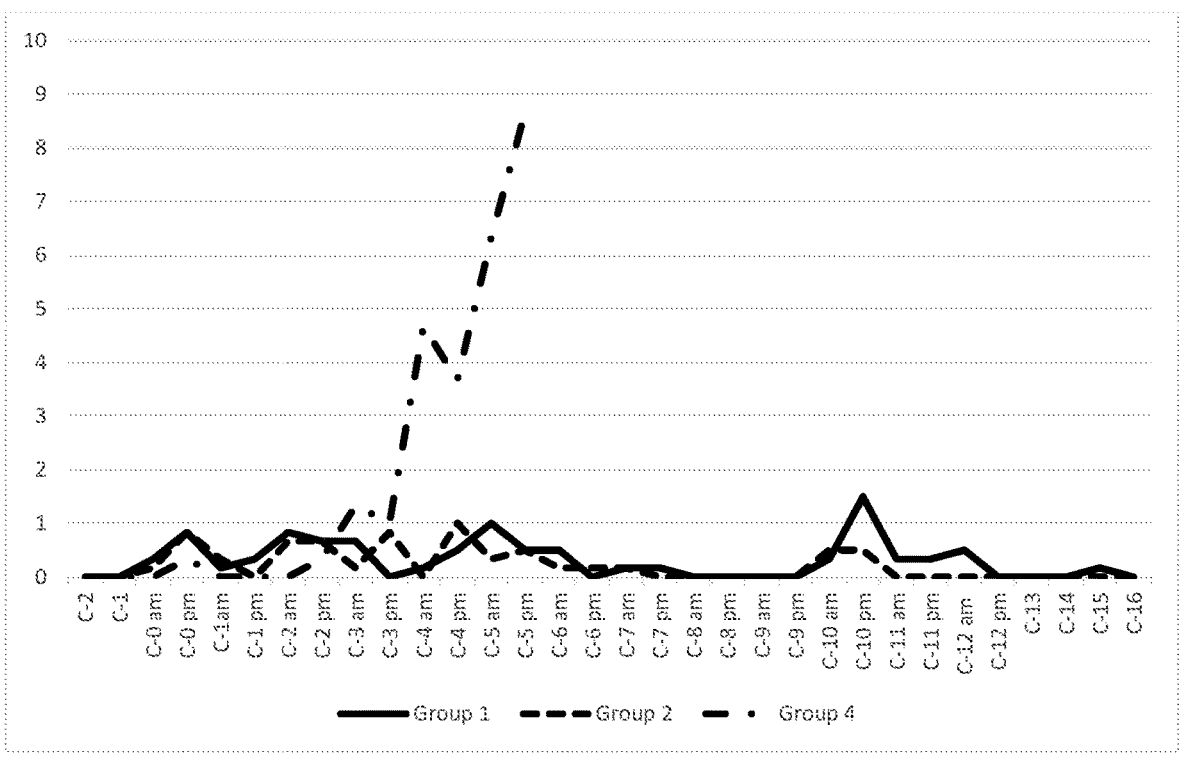
FIG. 7 shows clinical scores of pigs immunized at The Pirbright Institute with attenuated strain OURT88/3 at different days post-challenge with OURT88/1 virulent isolate according to an embodiment.
Figure 8:
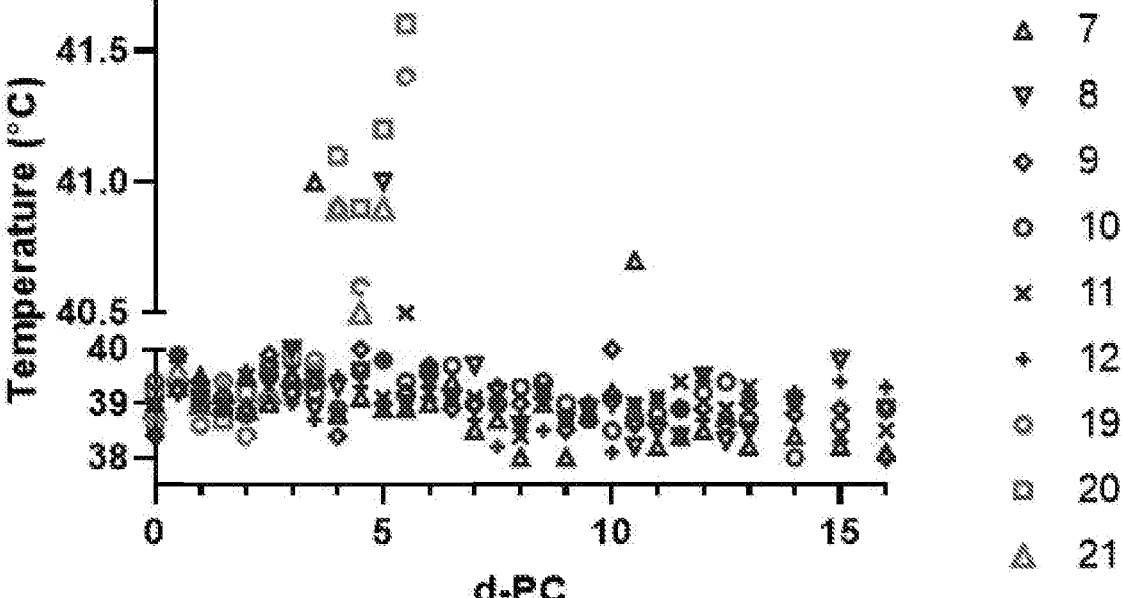
FIG. 8 shows temperatures following immunization of pigs with OURT88/3 passaged in ZMAC-4 cells according to an embodiment.
Figure 9:
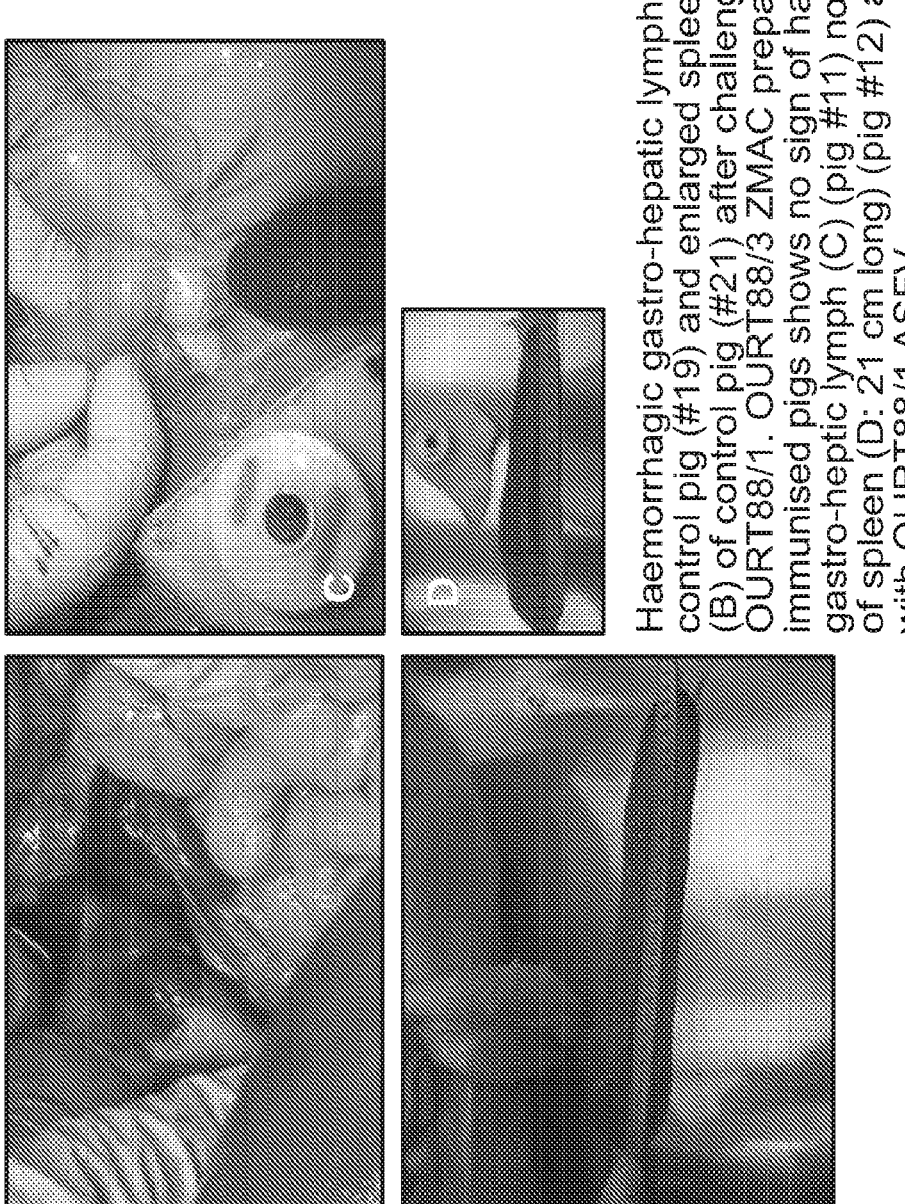
FIG. 9 shows post-mortem pig organs challenged with virulent strain OURT88/1 at The Pirbright Institute either after immunization with strain OURT88/3 or not immunized with OURT88/3 according to an embodiment.

Referring now to FIG. 7, all of the pigs immunized with the OURT88/3 passaged in ZMAC-4 cells (Group 2) and the Group 1 pigs survived the challenge and were euthanized between 16 and 18 days post-challenge. Clinical scores were very low post-immunization for the Group 1 and Group 2 pigs. The x-axis in FIG. 7 shows days post-challenge, and the y-axis shows clinical scores. Referring now to FIG. 8, pig 11 had a temperature of 40 on day 3 post-immunization and 40.2 on day 15 post-immunization. No other temperatures above 40.0° C. were observed. After challenge, pig 7 developed a temperature of 41° C. at day 3 post-challenge and 40.7 at day 10 post-challenge. Pig 9 had a temperature of 40 at day 5 post-challenge. Pig 10 had a temperature of 40.1 on the day of challenge, and pig 11 had a temperature of 40. 1 on day 4 and 40.5 on day 5 post-challenge. All pigs survived until termination at day 16 to 18 post-challenge. Two pigs (9 and 11) developed skin swellings or lameness and were treated with antibiotics which resolved these issues. Referring now to FIG. 9, post-mortem examination of the Group 1 and Group 2 pigs showed no macroscopic lesions (i.e., no hemorrhagic signs) nor enlargement of spleen typical of ASF (See C and D of FIG. 9).

Referring back to FIG. 8, in contrast to the Group 1 and Group 2 pigs, the control non-immune pigs (Group 4) all developed temperatures above 40.5 by day 4 post-challenge accompanied by lethargy and reduced or no eating. In addition, all Group 4 pigs showed skin reddening around the ear. Referring now to FIG. 11, all pigs in Group 4 (19, 20, and 21) were euthanized on day 5 post-challenge. Referring back to FIG. 7, Group 4 pigs developed typical clinical signs of ASFV from 3 to 4 days post-infection. Referring back to FIG. 9, post-mortem examination of the Group 4 pigs revealed signs typical of acute ASFV including hemorrhages in several lymph nodes (See A in FIG. 9) and enlarged and hemorrhagic spleens (See B in FIG. 9).

Referring now to FIG. 10, the y axis shows a log 10 scale (using triangles, a diamond, a circle, an "x," and a plus sign ("+") labeled 7-12, respectively) genome copies per ml of whole blood in pigs immunized with ZMAC cell-passaged OURT88/3 before and after challenge with virulent OURT88/1 strain. The levels in control non-immune pigs are shown in (using a circle, a square, and a triangle labeled C19, C20, and C21, respectively). The x-axis shows days post-immunization (PI) or post-challenge (PC). Referring back to FIG. 8, the y-axis shows the rectal temperature of different immunized pigs (using triangles, a diamond, a circle, an "x," and a plus sign ("+") labeled 7-12, respectively) post-challenge and of the control non-immune pigs (using a circle, a square, and a triangle labeled 19-21, respectively).

To monitor replication of the virus, as stated herein, blood samples were collected at weekly intervals before challenge and at 3 day intervals post-challenge to measure levels of virus genome by qPCR. Referring now to FIG. 11, the results showed four pigs (7, 8, 9, 10) from the group immunized with the OURT88/3 passaged in ZMAC-4 cells (Group 2) had low levels of virus genome (between $10^2$ and $10^4$ genome copies per ml) in blood before challenge. The x axis indicates days post-immunization or challenge, and the y axis shows virus genome copies per ml of blood. Error bars show standard deviation from 4 technical replicates. Samples from the same pigs are linked by solid lines. Squares show pigs from Group 2, stars show pigs from Group 1, and triangles show control pigs not immunized with OURT88/3 (Group 4). After challenge, 4 pigs had detectable virus genome. Of these pigs, 12 had $10^5$ at day 3 post-challenge and all other positive samples were $10^3$ or lower. Analysis of samples from spleen and tonsil detected no virus genome in tissues from any of the immunized and challenged pigs (Groups 1 and 2). In contrast, pigs in the control group (Group 4) developed high levels of virus in blood at day 3 post-challenge (3 to $8\times10^6$ TCID$_{50}$/m) rising to $8\times10^7$ to $2\times10^8$ TCID$_{50}$/ml) by day 5 or 6 post-challenge. The control pigs (Group 4) also had high levels of virus genome in spleen at termination ($5\times10^3$ to $2.7\times10^4$ per mg). In conclusion, pigs immunized with the OURT88/3 passaged in ZMAC-4 cells (Group 2) were all protected against challenge with the virulent isolate OURT88/1.

DISCUSSION

Here, the inventors show that the ZMAC-4 porcine macrophage cell line is susceptible to infection with ASFV field isolates and that the virus replicates with similar dynamics and to similar titers as in primary porcine macrophages. The lack of porcine macrophage cell lines resembling the in vivo target cells for ASFV replication has restricted research on the virus host interactions, limited the development of live attenuated vaccines, and made virus diagnosis more complex. The main target cells for ASFV replication in vivo are monocytes and macrophages. In cell culture, those cells that express markers characteristic of intermediate and late stages of differentiation are susceptible to infection. Although CD163 was first suggested to be required for infection, subsequent studies showed that monocytes that didn't express CD163 could also be infected. Gene-edited pigs lacking CD163 were fully susceptible to infection. Monocytes and macrophages from these pigs were also susceptible to infection proving that CD163 is not required. The availability of a suitable macrophage cell line will facilitate research by providing a genetically homogenous source of cells avoiding the large variation associated with primary cells from different outbred pigs. Research directed at understanding host factors that restrict virus replication and virus modulation of host cell function including evasion of host defenses will also be facilitated.

Importantly, availability of a porcine macrophage cell line can also replace the need for primary porcine cells for virus diagnosis and isolation. The inventors showed that titration of virus in ZMAC-4 cells provided similar results to primary porcine bone marrow cells and that both the gold standard hemadsorption assay and immunofluorescence for determining virus titers can be used with these cells. Thus, the ZMAC-4 cells can be an effective alternative to the use of primary macrophage cultures for ASFV infection. The inventors also demonstrated that passage of the live attenuated ASFV strain OURT88/3 in ZMAC-4 cells over 12 passages did not increase the clinical signs or viremia that resulted post-immunization or post-challenge compared to the OURT88/3 virus that hadn't been passaged in a study carried out in parallel or compared to other experiments in which OURT88/3 was delivered by the same route and dose.

OURT88/3 and several other field strains of ASFV grow to high titers in ZMAC-4 cells, similar to those obtained in primary macrophages, and without an adaptation process. Together the results prove that the ZMAC-4 cells provide an alternative to primary macrophages or other cells lines for ASFV diagnosis and vaccine production.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

What is claimed is:

1. A method for generating progeny of an African Swine Fever (ASF) virus, the method comprising:
providing an isolated or purified fetal porcine lung alveolar macrophage cell capable of replicating the ASF virus, wherein the cell is cultured for at least 5 passages;
exposing the cell to the ASF virus; and
allowing the ASF virus to replicate in the cell;
thereby generating progeny of the ASF virus.

2. The method of claim 1, further comprising contacting the cell with a growth factor composition.

3. The method of claim 2, wherein the growth factor composition comprises macrophage colony stimulating factor (MCSF) or granulocyte-macrophage colony stimulating factor (GMCSF).

4. A method for producing an ASF vaccine, the method comprising:
providing a modified-live virus (MLV) strain of ASF virus; and
growing the MLV strain in an isolated or purified fetal porcine lung alveolar macrophage cell capable of replicating the ASF MLV strain.

5. The method of claim 4, further comprising contacting the cell with a growth factor composition.

6. The method of claim 5, wherein the growth factor composition comprises macrophage colony stimulating factor (MCSF) or granulocyte-macrophage colony stimulating factor (GMCSF).

7. The method of claim 4, wherein the cell is obtained from a porcine fetal subject from about 30 to about 90 days of gestational age.

8. A method for growing an ASF virus, the method comprising:
isolating a fetal porcine lung alveolar macrophage cell from a porcine fetal lung comprising providing a porcine fetal subject, obtaining a cell-containing bronchoalveolar lavage sample from the subject, and separating the macrophage cell from the sample;
culturing the cell; and
contacting the cell with the ASF virus so as to allow viral replication;
thereby growing the ASF virus.

9. The method of claim 8, wherein the culturing comprises passaging the cell for at least 5 passages, culturing or passaging the cell for at least 10 passages, culturing or passaging the cell for at least 20 passages, growing the cell for at least 10 days of continuous culture, or a combination thereof.

10. The method of claim 8, wherein the culturing comprises contacting the cell with a growth factor composition.

11. The method of claim 10, wherein the growth factor composition comprises macrophage colony stimulating factor (MCSF) or granulocyte-macrophage colony stimulating factor (GMCSF).

12. The method of claim 8, wherein the cell is obtained from a porcine fetal subject from about 30 to about 90 days of gestational age.

13. A method for detecting the presence of an ASF virus in a porcine subject, the method comprising:

replicating the ASF virus using an isolated or purified fetal porcine lung alveolar macrophage cell, wherein the cell is cultured for at least 5 passages;

contacting the cell with a sample;

incubating the cell under suitable conditions; and detecting the presence of the ASF virus in the cell.

14. The method of claim 13, further comprising contacting the cell with a growth factor composition, wherein the growth factor composition comprises macrophage colony stimulating factor (MCSF) or granulocyte-macrophage colony stimulating factor (GMCSF).

15. The method of claim 13, wherein the cell is obtained from a porcine fetal subject from about 30 to about 90 days of gestational age.

16. The method of claim 13, wherein the sample is selected from the group consisting of blood, serum, plasma, lymph, saliva, nasal secretions, feces, urine, semen, sputum, cerebrospinal fluid, tears, mucus, sweat, milk, and tissue cells, wherein the tissues cells are selected from the group consisting of thymus, lymph node, spleen, bone marrow, and tonsil.

17. The method of claim 13, wherein the detecting comprises utilizing a hemadsorption assay or immunofluorescence.

18. A vaccine comprising the progeny of the ASF virus of claim 1 in a carrier and an adjuvant.

19. A method of eliciting an immune response against ASFV in a porcine, the method comprising administering an effective amount of the vaccine of claim 18 to the porcine, wherein the route of administration is selected from the group consisting of parenterally, orally, intranasally, and mucosally.

20. The method of claim 1, wherein the ASF virus is selected from OURT88/3 or NH/P68 genotype I non-hemadsorbing attenuated ASFV strains; virulent strains genotype I OURT88/1 or Benin97/1; Georgia genotype II; Malawi LIL 20/1 genotype VIII; or moderately virulent Dominican Republic strains Tengani, MOZ 94/1, or ZOM 2/84.

* * * * *